US010654899B2

(12) United States Patent
Liljeqvist

(10) Patent No.: US 10,654,899 B2
(45) Date of Patent: May 19, 2020

(54) TRUNCATED GLYCOPROTEIN G OF HERPES SIMPLEX VIRUS 2

(71) Applicant: SIMPLEXIA AB, Göteborg (SE)

(72) Inventor: Jan-Åke Liljeqvist, Göteborg (SE)

(73) Assignee: SIMPLEXIA AB, Göteborg (SE)

( * ) Notice: Subject to any disclaimer, the term of this patent is extended or adjusted under 35 U.S.C. 154(b) by 0 days.

(21) Appl. No.: 16/072,499

(22) PCT Filed: Jan. 31, 2017

(86) PCT No.: PCT/EP2017/052070
§ 371 (c)(1),
(2) Date: Jul. 24, 2018

(87) PCT Pub. No.: WO2017/134061
PCT Pub. Date: Aug. 10, 2017

(65) Prior Publication Data

US 2019/0031723 A1 Jan. 31, 2019

(30) Foreign Application Priority Data

Feb. 1, 2016 (SE) ...................................... 1650122

(51) Int. Cl.

| | |
|---|---|
| ***C07K 14/005*** | (2006.01) |
| ***G01N 33/569*** | (2006.01) |
| ***A61K 39/12*** | (2006.01) |
| ***A61K 39/00*** | (2006.01) |

(52) U.S. Cl.
CPC ............ *C07K 14/005* (2013.01); *A61K 39/12* (2013.01); *G01N 33/56994* (2013.01); *A61K 39/00* (2013.01); *A61K 2039/70* (2013.01); *C12N 2710/16022* (2013.01); *C12N 2710/16034* (2013.01); *C12N 2710/16071* (2013.01); *G01N 2333/035* (2013.01)

(58) Field of Classification Search
CPC .... C07K 14/005; C07K 16/085; A61K 39/12; A61K 2039/70; A61K 39/00; A61K 2300/00; A61K 39/42; A61K 39/245; A61K 38/162; G01N 33/56994; G01N 2333/035; C12N 2710/16071; C12N 2710/16034; C12N 2710/16022; C12N 7/00; C12N 2710/16734
See application file for complete search history.

(56) References Cited

U.S. PATENT DOCUMENTS

| | | | | |
|---|---|---|---|---|
| 5,665,537 A | | 9/1997 | Parkes et al. | |
| 5,965,354 A | * | 10/1999 | Burke .................... | C12Q 1/705 424/204.1 |

FOREIGN PATENT DOCUMENTS

| | | |
|---|---|---|
| WO | WO 96/17938 A1 | 6/1996 |
| WO | WO 97/05488 A1 | 2/1997 |
| WO | WO 98/03543 A1 | 1/1998 |
| WO | WO 2010/135747 A1 | 11/2010 |
| WO | WO 2012/074881 A2 | 6/2012 |

OTHER PUBLICATIONS

Adamiak B, Ekblad M, Bergstrom T, Ferro V, Trybala E. Glycoprotein G [Human alphaherpesvirus 2]. GenBank: ABU45440.1, Dep. Nov. 29, 2007.*
Altschul, Stephen F. et al.; "Gapped BLAST and PSI-BLAST: a new generation of protein database search programs"; Nucleic Acids Res.; 1997; vol. 25; No. 17; pp. 3389-3402.
Belshe, Robert B. et al.; "Efficacy Results of a Trial of a Herpes Simplex Vaccine"; N. Engl J Med; Jan. 2012; vol. 366(1); pp. 34-43.
Boucher et al.; Clin Diagn Virol, 1993, vol. 1, 29 (On Order).
Corey, Lawrence et al.; "Recombinant Glycoprotein Vaccine for the Prevention of Genital HSV-2 Infection"; JAMA; Jul. 1999; vol. 281; No. 4; pp. 331-340.
Devereux, John et al.; "A comprehensive set of sequence analysis programs for the VAX", Nucleic Acids Res.; 1984; vol. 12; No. 1; pp. 387-395.
Görander, Staffan et al.; "Mature Glycoprotein G Presents High Performance in Diagnosing Herpes Simplex Virus Type 2 Infection in Sera of Different Tanzanian Cohorts"; Clin. Vaccine Immunol.; Jun. 2006; vol. 13; No. 6; pp. 633-639.

(Continued)

*Primary Examiner* — Rachel B Gill
(74) *Attorney, Agent, or Firm* — Lewis Roca Rothgerber Christie LLP

(57) ABSTRACT

The present invention relates to a protein comprising a truncated version of the HSV-2 protein mg G-2, said protein comprising: (i) an extracellular region of mg G-2 (EX-mg G-2), or a truncated version thereof, of at least 285 amino acids; said extracellular region or truncated version thereof having at least 90%, 95%, 96%, 97%, 98% or 99% sequence identity (% SI) to a peptide fragment of the corresponding length present in SEQ ID NO: 3; (ii) a truncated transmembrane region of mg G-2 (t-TMR-mg G-2) of 2 to 15 amino acids; said truncated transmembrane region having at least 90% sequence identity (% SI) to a peptide fragment of the corresponding length present in SEQ ID NO: 6; and (iii) an intracellular region of mg G-2 (IC-mg G-2), or a truncated version thereof, of at least 18 amino acids; said intracellular region or truncated version thereof having at least 90% or 95% sequence identity (% SI) to a peptide fragment of the corresponding length present in SEQ ID NO: 8.

19 Claims, 10 Drawing Sheets

Specification includes a Sequence Listing.

(56) References Cited

OTHER PUBLICATIONS

Görander, Staffan; "Functions of glycoprotein G of herpes simplex virus type 2"; Thesis 2010; University of Gothenburg; ISBN 978-91-628-8005-7; 58pp.
Grabowska, A. et al.; "Identification of type-specific domains within glycoprotein G of herpes simplex virus type 2 (HSV-2) recognized by the majority of patients infected with HSV-2, but not by those infected with HSV-1"; J Gen Virol.; 1999; vol. 80; pp. 1789-1798.
Harandi et al., 2001, Am J Reprod Immunol. vol. 46, 420 (On Order).
Iijima, Norifumi et al.; "Dendritic cells and B cells maximize mucosal Th1 memory response to herpes simplex virus"; J Exp Med.; vol. 205; No. 13; 2008; pp. 3041-3052.
Jeansson, Stig et al.; "Evaluation of Solubilized Herpes Simplex Virus Membrane Antigen by Enzyme-Linked Immunosorbent Assay"; J Clin Microbiol.; Nov. 1983; vol. 18; No. 5; pp. 1160-1166.
Liljeqvist, Jan-Ake et al.; "Localization of type-specific epitopes of herpes simplex virus type 2 glycoprotein G recognized by human and mouse antibodies"; Journal of General Virology; 1998; vol. 79; pp. 1215-1224.
Looker, Katharine J. et al.; "Global Estimates of Prevalent and Incident Herpes Simplex Virus Type 2 Infections in 2012"; PLoS One; Jan. 2015; vol. 10; e114989; 23pp.
Marsden et al., 1998, J Med Virol., vol. 56, 79 (On Order).
Myers, Eugene W. et al.; "Optimal alignments in linear space"; CABIOS; 1988; vol. 4; No. 1; pp. 11-17.
Olofsson, Sigvard et al.; "Unusual Lectin-Binding Properties of a Herpes Simplex Virus Type 1-Specific Glycoprotein"; J Virol.; May 1981; vol. 38; No. 2; pp. 564-570.
Parr and Parr, Int Rev Immunol., 2003, vol. 22, 43 (On Order).
Parr, E. L. et al.; "Immune responses and protection against vaginal infection after nasal or vaginal immunization with attenuated herpes simplex virus type-2"; Immunology; 1999; vol. 98; pp. 639-645.
Svennerholm, B. et al.; "Herpes Simplex Virus Type-Selective Enzyme-Linked Immunosorbent Assay with *Helix pomatia* Lectin-Purified Antigens"; J Clin Microbiol.; Feb. 1984; vol. 19; No. 2; pp. 235-239.
Thompson, Julie D. et al.; "CLUSTAL W: improving the sensitivity of progressive multiple sequence alignment through sequence weighting, position-specific gap penalties and weight matrix choice"; Nucleic Acids Res.; 1994; vol. 22; No. 22; pp. 4673-4680.
Tunbäack, Petra et al.; "Glycoprotein G of herpes simplex virus type 1: identification of type-specific epitopes by human antibodies"; J Gen Virol.; 2000; vol. 81; pp. 1033-1040.
Tunbäck, Petra et al.; "Type-Specific reactivity of anti-glycoprotein G antibodies from herpes simplex virus-infected individuals is maintained by single or dual type-specific residues"; J Gen Virol.; 2005; vol. 86; pp. 247-251.
Görander, Staffan et al., "Anti-Glycoprotein G Antibodies of Herpes Simplex Virus 2 Contribute to Complete Protection after Vaccination in Mice and Induce Antibody-Dependent Cellular Cytotoxicity and Complement-Mediated Cytolysis"; Viruses; 2014; vol. 6; pp. 4358-4372; doi:10.3390/v6114358.
Görander, Staffan et al., "Glycoprotein G of Herpes Simplex Virus 2 as a Novel Vaccine Antigen for Immunity to Genital and Neurological Disease"; Journal of Virology; Jul. 2012; vol. 86; No. 14; pp. 7544-7553.
Levi, Michael et al.; "Peptide Sequences of Glycoprotein G-2 Discriminate between Herpes Simplex Virus Type 2 (HSV-2) and HSV-1 Antibodies"; Clinical and Diagnostic Laboratory Immunology; May 1996; vol. 3; No. 3; pp. 265-269.
Manservigi, R. et al.; "Protection from Herpes Simplex Virus Type 1 Lethal and Latent Infections by Secreted Recombinant Glycoprotein B Constitutively Expressed in Human Cells with a BK Virus Episomal Vector"; Journal of Virology; Jan. 1990; vol. 64, No. 1; pp. 431-436.

* cited by examiner

SEQUENCE LISTING

<160> NUMBER OF SEQ ID NOS: 19

<210> SEQ ID NO 1
<211> LENGTH: 698
<212> TYPE: PRT
<213> ORGANISM: herpes simplex virus 2

<400> SEQUENCE: 1

Met His Ala Ile Ala Pro Arg Leu Leu Leu Leu Phe Val Leu Ser Gly
1               5                   10                  15

Leu Pro Gly Thr Arg Gly Gly Ser Gly Val Pro Gly Pro Ile Asn Pro
            20                  25                  30

Pro Asn Asn Asp Val Val Phe Pro Gly Gly Ser Pro Val Ala Gln Tyr
        35                  40                  45

Cys Tyr Ala Tyr Pro Arg Leu Asp Asp Pro Gly Pro Leu Gly Ser Ala
    50                  55                  60

Asp Ala Gly Arg Gln Asp Leu Pro Arg Arg Val Val Arg His Glu Pro
65                  70                  75                  80

Leu Gly Arg Ser Phe Leu Thr Gly Gly Leu Val Leu Leu Ala Pro Pro
                85                  90                  95

Val Arg Gly Phe Gly Ala Pro Asn Ala Thr Tyr Ala Ala Arg Val Thr
            100                 105                 110

Tyr Tyr Arg Leu Thr Arg Ala Cys Arg Gln Pro Ile Leu Leu Arg Gln
        115                 120                 125

Tyr Gly Gly Cys Arg Gly Gly Glu Pro Pro Ser Pro Lys Thr Cys Gly
    130                 135                 140

Ser Tyr Thr Tyr Thr Tyr Gln Gly Gly Gly Pro Pro Thr Arg Tyr Ala
145                 150                 155                 160

Leu Val Asn Ala Ser Leu Leu Val Pro Ile Trp Asp Arg Ala Ala Glu
                165                 170                 175

Thr Phe Glu Tyr Gln Ile Glu Leu Gly Gly Glu Leu His Val Gly Leu
            180                 185                 190

Leu Trp Val Glu Val Gly Gly Glu Gly Pro Gly Pro Thr Ala Pro Pro
        195                 200                 205

Gln Ala Ala Arg Ala Glu Gly Gly Pro Cys Val Pro Pro Val Pro Ala
    210                 215                 220

Gly Arg Pro Trp Arg Ser Val Pro Pro Val Trp Tyr Ser Ala Pro Asn
225                 230                 235                 240

Pro Gly Phe Arg Gly Leu Arg Phe Arg Glu Arg Cys Leu Pro Pro Gln
                245                 250                 255

-continued

```
Thr Pro Ala Ala Pro Ser Asp Leu Pro Arg Val Ala Phe Ala Pro Gln
            260                 265                 270

Ser Leu Leu Val Gly Ile Thr Gly Arg Thr Phe Ile Arg Met Ala Arg
        275                 280                 285

Pro Thr Glu Asp Val Gly Val Leu Pro Pro His Trp Ala Pro Gly Ala
    290                 295                 300

Leu Asp Asp Gly Pro Tyr Ala Pro Phe Pro Pro Arg Pro Arg Phe Arg
305                 310                 315                 320

Arg Ala Leu Arg Thr Asp Pro Glu Gly Val Asp Pro Asp Val Arg Ala
                325                 330                 335

Pro Leu Thr Gly Arg Arg Leu Met Ala Leu Thr Glu Asp Ala Ser Ser
            340                 345                 350

Asp Ser Pro Thr Ser Ala Pro Glu Lys Thr Pro Leu Pro Val Ser Ala
        355                 360                 365

Thr Ala Met Ala Pro Ser Val Asp Pro Ser Ala Glu Pro Thr Ala Pro
    370                 375                 380

Ala Thr Thr Thr Pro Pro Asp Glu Met Ala Thr Gln Ala Ala Thr Val
385                 390                 395                 400

Ala Val Thr Pro Glu Glu Thr Ala Val Ala Ser Pro Pro Ala Thr Ala
                405                 410                 415

Ser Val Glu Ser Ser Pro Leu Pro Ala Ala Ala Ala Thr Pro Gly Ala
            420                 425                 430

Gly His Thr Asn Thr Ser Ser Ala Pro Ala Ala Lys Thr Pro Pro Thr
        435                 440                 445

Thr Pro Ala Pro Thr Thr Pro Pro Pro Thr Ser Thr His Ala Thr Pro
    450                 455                 460

Arg Pro Thr Thr Pro Gly Pro Gln Thr Thr Pro Pro Gly Pro Ala Thr
465                 470                 475                 480

Pro Gly Pro Val Gly Ala Ser Ala Ala Pro Thr Ala Asp Ser Pro Leu
                485                 490                 495

Thr Ala Ser Pro Pro Ala Thr Ala Pro Gly Pro Ser Ala Ala Asn Val
            500                 505                 510

Ser Val Ala Ala Thr Thr Ala Thr Pro Gly Thr Arg Gly Thr Ala Arg
        515                 520                 525

Thr Pro Pro Thr Asp Pro Lys Thr His Pro His Gly Pro Ala Asp Ala
    530                 535                 540

Pro Pro Gly Ser Pro Ala Pro Pro Pro Pro Glu His Arg Gly Gly Pro
545                 550                 555                 560

Glu Glu Phe Glu Gly Ala Gly Asp Gly Glu Pro Pro Asp Asp Asp Asp
                565                 570                 575

Ser Ala Thr Gly Leu Ala Phe Arg Thr Pro Asn Pro Asn Lys Pro Pro
            580                 585                 590

Pro Ala Arg Pro Gly Pro Ile Arg Pro Thr Leu Pro Pro Gly Ile Leu
        595                 600                 605

Gly Pro Leu Ala Pro Asn Thr Pro Arg Pro Pro Ala Gln Ala Pro Ala
    610                 615                 620

Lys Asp Met Pro Ser Gly Pro Thr Pro Gln His Ile Pro Leu Phe Trp
625                 630                 635                 640

Phe Leu Thr Ala Ser Pro Ala Leu Asp Ile Leu Phe Ile Ile Ser Thr
                645                 650                 655

Thr Ile His Thr Ala Ala Phe Val Cys Leu Val Ala Leu Ala Ala Gln
            660                 665                 670
```

```
Leu Trp Arg Gly Arg Ala Gly Arg Arg Arg Tyr Ala His Pro Ser Val
        675                 680                 685

Arg Tyr Val Cys Leu Pro Pro Glu Arg Asp
    690                 695


<210> SEQ ID NO 2
<211> LENGTH: 354
<212> TYPE: PRT
<213> ORGANISM: herpes simplex virus 2

<400> SEQUENCE: 2

Ala Leu Thr Glu Asp Ala Ser Ser Asp Ser Pro Thr Ser Ala Pro Glu
1               5                   10                  15

Lys Thr Pro Leu Pro Val Ser Ala Thr Ala Met Ala Pro Ser Val Asp
            20                  25                  30

Pro Ser Ala Glu Pro Thr Ala Pro Ala Thr Thr Thr Pro Pro Asp Glu
        35                  40                  45

Met Ala Thr Gln Ala Ala Thr Val Ala Val Thr Pro Glu Glu Thr Ala
    50                  55                  60

Val Ala Ser Pro Pro Ala Thr Ala Ser Val Glu Ser Ser Pro Leu Pro
65                  70                  75                  80

Ala Ala Ala Ala Thr Pro Gly Ala Gly His Thr Asn Thr Ser Ser Ala
                85                  90                  95

Pro Ala Ala Lys Thr Pro Pro Thr Thr Pro Ala Pro Thr Thr Pro Pro
            100                 105                 110

Pro Thr Ser Thr His Ala Thr Pro Arg Pro Thr Thr Pro Gly Pro Gln
        115                 120                 125

Thr Thr Pro Pro Gly Pro Ala Thr Pro Gly Pro Val Gly Ala Ser Ala
    130                 135                 140

Ala Pro Thr Ala Asp Ser Pro Leu Thr Ala Ser Pro Pro Ala Thr Ala
145                 150                 155                 160

Pro Gly Pro Ser Ala Ala Asn Val Ser Val Ala Ala Thr Thr Ala Thr
                165                 170                 175

Pro Gly Thr Arg Gly Thr Ala Arg Thr Pro Pro Thr Asp Pro Lys Thr
            180                 185                 190

His Pro His Gly Pro Ala Asp Ala Pro Pro Gly Ser Pro Ala Pro Pro
        195                 200                 205

Pro Pro Glu His Arg Gly Gly Pro Glu Glu Phe Glu Gly Ala Gly Asp
    210                 215                 220

Gly Glu Pro Pro Asp Asp Asp Asp Ser Ala Thr Gly Leu Ala Phe Arg
225                 230                 235                 240

Thr Pro Asn Pro Asn Lys Pro Pro Pro Ala Arg Pro Gly Pro Ile Arg
                245                 250                 255

Pro Thr Leu Pro Pro Gly Ile Leu Gly Pro Leu Ala Pro Asn Thr Pro
            260                 265                 270

Arg Pro Pro Ala Gln Ala Pro Ala Lys Asp Met Pro Ser Gly Pro Thr
        275                 280                 285

Pro Gln His Ile Pro Leu Phe Trp Phe Leu Thr Ala Ser Pro Ala Leu
    290                 295                 300

Asp Ile Leu Phe Ile Ile Ser Thr Thr Ile His Thr Ala Ala Phe Val
305                 310                 315                 320

Cys Leu Val Ala Leu Ala Ala Gln Leu Trp Arg Gly Arg Ala Gly Arg
                325                 330                 335

Arg Arg Tyr Ala His Pro Ser Val Arg Tyr Val Cys Leu Pro Pro Glu
            340                 345                 350
```

-continued

Arg Asp

<210> SEQ ID NO 3
<211> LENGTH: 305
<212> TYPE: PRT
<213> ORGANISM: herpes simplex virus 2

<400> SEQUENCE: 3

Ala Leu Thr Glu Asp Ala Ser Ser Asp Ser Pro Thr Ser Ala Pro Glu
1 5 10 15

Lys Thr Pro Leu Pro Val Ser Ala Thr Ala Met Ala Pro Ser Val Asp
20 25 30

Pro Ser Ala Glu Pro Thr Ala Pro Ala Thr Thr Thr Pro Pro Asp Glu
35 40 45

Met Ala Thr Gln Ala Ala Thr Val Ala Val Thr Pro Glu Glu Thr Ala
50 55 60

Val Ala Ser Pro Pro Ala Thr Ala Ser Val Glu Ser Ser Pro Leu Pro
65 70 75 80

Ala Ala Ala Ala Thr Pro Gly Ala Gly His Thr Asn Thr Ser Ser Ala
85 90 95

Pro Ala Ala Lys Thr Pro Pro Thr Thr Pro Ala Pro Thr Thr Pro Pro
100 105 110

Pro Thr Ser Thr His Ala Thr Pro Arg Pro Thr Thr Pro Gly Pro Gln
115 120 125

Thr Thr Pro Pro Gly Pro Ala Thr Pro Gly Pro Val Gly Ala Ser Ala
130 135 140

Ala Pro Thr Ala Asp Ser Pro Leu Thr Ala Ser Pro Pro Ala Thr Ala
145 150 155 160

Pro Gly Pro Ser Ala Ala Asn Val Ser Val Ala Ala Thr Thr Ala Thr
165 170 175

Pro Gly Thr Arg Gly Thr Ala Arg Thr Pro Pro Thr Asp Pro Lys Thr
180 185 190

His Pro His Gly Pro Ala Asp Ala Pro Pro Gly Ser Pro Ala Pro Pro
195 200 205

Pro Pro Glu His Arg Gly Gly Pro Glu Glu Phe Glu Gly Ala Gly Asp
210 215 220

Gly Glu Pro Pro Asp Asp Asp Asp Ser Ala Thr Gly Leu Ala Phe Arg
225 230 235 240

Thr Pro Asn Pro Asn Lys Pro Pro Pro Ala Arg Pro Gly Pro Ile Arg
245 250 255

Pro Thr Leu Pro Pro Gly Ile Leu Gly Pro Leu Ala Pro Asn Thr Pro
260 265 270

Arg Pro Pro Ala Gln Ala Pro Ala Lys Asp Met Pro Ser Gly Pro Thr
275 280 285

Pro Gln His Ile Pro Leu Phe Trp Phe Leu Thr Ala Ser Pro Ala Leu
290 295 300

Asp
305

<210> SEQ ID NO 4
<211> LENGTH: 333
<212> TYPE: PRT
<213> ORGANISM: Artificial Sequence
<220> FEATURE:
<223> OTHER INFORMATION: EXCT0-mgG-2

<400> SEQUENCE: 4

```
Ala Leu Thr Glu Asp Ala Ser Ser Asp Ser Pro Thr Ser Ala Pro Glu
1               5                   10                  15

Lys Thr Pro Leu Pro Val Ser Ala Thr Ala Met Ala Pro Ser Val Asp
            20                  25                  30

Pro Ser Ala Glu Pro Thr Ala Pro Ala Thr Thr Thr Pro Pro Asp Glu
        35                  40                  45

Met Ala Thr Gln Ala Ala Thr Val Ala Val Thr Pro Glu Glu Thr Ala
    50                  55                  60

Val Ala Ser Pro Pro Ala Thr Ala Ser Val Glu Ser Ser Pro Leu Pro
65                  70                  75                  80

Ala Ala Ala Ala Thr Pro Gly Ala Gly His Thr Asn Thr Ser Ser Ala
                85                  90                  95

Pro Ala Ala Lys Thr Pro Pro Thr Thr Pro Ala Pro Thr Thr Pro Pro
            100                 105                 110

Pro Thr Ser Thr His Ala Thr Pro Arg Pro Thr Thr Pro Gly Pro Gln
        115                 120                 125

Thr Thr Pro Pro Gly Pro Ala Thr Pro Gly Pro Val Gly Ala Ser Ala
    130                 135                 140

Ala Pro Thr Ala Asp Ser Pro Leu Thr Ala Ser Pro Pro Ala Thr Ala
145                 150                 155                 160

Pro Gly Pro Ser Ala Ala Asn Val Ser Val Ala Ala Thr Thr Ala Thr
                165                 170                 175

Pro Gly Thr Arg Gly Thr Ala Arg Thr Pro Pro Thr Asp Pro Lys Thr
            180                 185                 190

His Pro His Gly Pro Ala Asp Ala Pro Pro Gly Ser Pro Ala Pro Pro
        195                 200                 205

Pro Pro Glu His Arg Gly Gly Pro Glu Glu Phe Glu Gly Ala Gly Asp
    210                 215                 220

Gly Glu Pro Pro Asp Asp Asp Asp Ser Ala Thr Gly Leu Ala Phe Arg
225                 230                 235                 240

Thr Pro Asn Pro Asn Lys Pro Pro Pro Ala Arg Pro Gly Pro Ile Arg
                245                 250                 255

Pro Thr Leu Pro Pro Gly Ile Leu Gly Pro Leu Ala Pro Asn Thr Pro
            260                 265                 270

Arg Pro Pro Ala Gln Ala Pro Ala Lys Asp Met Pro Ser Gly Pro Thr
        275                 280                 285

Pro Gln His Ile Pro Leu Phe Trp Phe Leu Thr Ala Ser Pro Ala Leu
    290                 295                 300

Asp Ala Gln Leu Trp Arg Gly Arg Ala Gly Arg Arg Arg Tyr Ala His
305                 310                 315                 320

Pro Ser Val Arg Tyr Val Cys Leu Pro Pro Glu Arg Asp
                325                 330
```

<210> SEQ ID NO 5
<211> LENGTH: 337
<212> TYPE: PRT
<213> ORGANISM: Artificial Sequence
<220> FEATURE:
<223> OTHER INFORMATION: EXCT4-mgG-2

<400> SEQUENCE: 5

```
Ala Leu Thr Glu Asp Ala Ser Ser Asp Ser Pro Thr Ser Ala Pro Glu
1               5                   10                  15
```

-continued

```
Lys Thr Pro Leu Pro Val Ser Ala Thr Ala Met Ala Pro Ser Val Asp
            20                  25                  30

Pro Ser Ala Glu Pro Thr Ala Pro Ala Thr Thr Thr Pro Pro Asp Glu
        35                  40                  45

Met Ala Thr Gln Ala Ala Thr Val Ala Val Thr Pro Glu Glu Thr Ala
    50                  55                  60

Val Ala Ser Pro Pro Ala Thr Ala Ser Val Glu Ser Ser Pro Leu Pro
65                  70                  75                  80

Ala Ala Ala Ala Thr Pro Gly Ala Gly His Thr Asn Thr Ser Ser Ala
                85                  90                  95

Pro Ala Ala Lys Thr Pro Pro Thr Thr Pro Ala Pro Thr Thr Pro Pro
            100                 105                 110

Pro Thr Ser Thr His Ala Thr Pro Arg Pro Thr Thr Pro Gly Pro Gln
        115                 120                 125

Thr Thr Pro Pro Gly Pro Ala Thr Pro Gly Pro Val Gly Ala Ser Ala
    130                 135                 140

Ala Pro Thr Ala Asp Ser Pro Leu Thr Ala Ser Pro Pro Ala Thr Ala
145                 150                 155                 160

Pro Gly Pro Ser Ala Ala Asn Val Ser Val Ala Ala Thr Thr Ala Thr
                165                 170                 175

Pro Gly Thr Arg Gly Thr Ala Arg Thr Pro Pro Thr Asp Pro Lys Thr
            180                 185                 190

His Pro His Gly Pro Ala Asp Ala Pro Pro Gly Ser Pro Ala Pro Pro
        195                 200                 205

Pro Pro Glu His Arg Gly Gly Pro Glu Glu Phe Glu Gly Ala Gly Asp
    210                 215                 220

Gly Glu Pro Pro Asp Asp Asp Asp Ser Ala Thr Gly Leu Ala Phe Arg
225                 230                 235                 240

Thr Pro Asn Pro Asn Lys Pro Pro Pro Ala Arg Pro Gly Pro Ile Arg
                245                 250                 255

Pro Thr Leu Pro Pro Gly Ile Leu Gly Pro Leu Ala Pro Asn Thr Pro
            260                 265                 270

Arg Pro Pro Ala Gln Ala Pro Ala Lys Asp Met Pro Ser Gly Pro Thr
        275                 280                 285

Pro Gln His Ile Pro Leu Phe Trp Phe Leu Thr Ala Ser Pro Ala Leu
    290                 295                 300

Asp Val Ala Leu Ala Ala Gln Leu Trp Arg Gly Arg Ala Gly Arg Arg
305                 310                 315                 320

Arg Tyr Ala His Pro Ser Val Arg Tyr Val Cys Leu Pro Pro Glu Arg
                325                 330                 335

Asp
```

<210> SEQ ID NO 6
<211> LENGTH: 21
<212> TYPE: PRT
<213> ORGANISM: herpes simplex virus 2

<400> SEQUENCE: 6

```
Ile Leu Phe Ile Ile Ser Thr Thr Ile His Thr Ala Ala Phe Val Cys
1               5                   10                  15

Leu Val Ala Leu Ala
            20
```

<210> SEQ ID NO 7

<211> LENGTH: 4
<212> TYPE: PRT
<213> ORGANISM: herpes simplex virus 2

<400> SEQUENCE: 7

Val Ala Leu Ala
1

<210> SEQ ID NO 8
<211> LENGTH: 28
<212> TYPE: PRT
<213> ORGANISM: herpes simplex virus 2

<400> SEQUENCE: 8

Ala Gln Leu Trp Arg Gly Arg Ala Gly Arg Arg Arg Tyr Ala His Pro
1 5 10 15

Ser Val Arg Tyr Val Cys Leu Pro Pro Glu Arg Asp
20 25

<210> SEQ ID NO 9
<211> LENGTH: 10
<212> TYPE: PRT
<213> ORGANISM: herpes simplex virus 2

<400> SEQUENCE: 9

Ile Leu Phe Ile Ile Ser Thr Thr Ile His
1 5 10

<210> SEQ ID NO 10
<211> LENGTH: 11
<212> TYPE: PRT
<213> ORGANISM: herpes simplex virus 2

<400> SEQUENCE: 10

Thr Ala Ala Phe Val Cys Leu Val Ala Leu Ala
1 5 10

<210> SEQ ID NO 11
<211> LENGTH: 5
<212> TYPE: PRT
<213> ORGANISM: herpes simplex virus 2

<400> SEQUENCE: 11

Ile Leu Phe Ile Ile
1 5

<210> SEQ ID NO 12
<211> LENGTH: 5
<212> TYPE: PRT
<213> ORGANISM: herpes simplex virus 2

<400> SEQUENCE: 12

Leu Val Ala Leu Ala
1 5

<210> SEQ ID NO 13
<211> LENGTH: 2097
<212> TYPE: DNA
<213> ORGANISM: herpes simplex virus 2

<400> SEQUENCE: 13
atgcacgcca tcgctcccag gttgcttctt ctttttgttc tttctggtct tccggggaca 60
cgcggcgggt cgggtgtccc cggaccaatt aatcccccca acaacgatgt tgttttcccg 120

-continued

```
ggaggttccc ccgtggctca atattgttat gcctatcccc ggttggacga tcccgggccc    180

ttgggttccg cggacgccgg gcggcaagac ctgccccggc gcgtcgtccg tcacgagccc    240

ctgggccgct cgttcctcac ggggggctg gttttgctgg cgccgccggt acgcggattt    300

ggcgcaccca acgcaacgta tgcggcccgt gtgacgtact accggctcac ccgcgcctgc    360

cgtcagccca tcctccttcg gcagtatgga gggtgtcgcg gcggcgagcc gccgtcccca    420

aagacgtgcg ggtcgtacac gtacacgtac cagggcggcg ggcctccgac ccggtacgct    480

ctcgtaaatg cttccctgct ggtgccgatc tgggaccgcg ccgcggagac attcgagtac    540

cagatcgaac tcggcggcga gctgcacgtg ggtctgttgt gggtagaggt gggcggggag    600

ggccccggcc ccaccgcccc cccacaggcg gcgcgtgcgg agggcggccc gtgcgtcccc    660

ccggtccccg cgggccgccc gtggcgctcg gtgcccccgg tatggtattc cgcccccaac    720

cccgggtttc gtggcctgcg tttccgggag cgctgtctgc ccccacagac gcccgccgcc    780

cccagcgacc taccacgcgt cgcttttgct ccccagagcc tgctggtggg gattacgggc    840

cgcacgttta ttcggatggc acgacccacg gaagacgtcg gggtcctgcc accccattgg    900

gcccccgggg ccctagatga cggtccgtac gccccccttcc caccccgccc gcggtttcga    960

cgcgccctgc ggacagaccc cgagggggtc gaccccgacg ttcgggcccc cctaaccggg   1020

cggcgcctca tggccttgac cgaggacgcg tcctccgatt cgcctacgtc cgctccggag   1080

aagacgcccc tccctgtgtc ggccaccgcc atggcgccct cagtcgaccc aagcgcggaa   1140

ccgaccgccc ccgcaaccac tactcccccc gacgagatgg ccacacaagc cgcaacggtc   1200

gccgttacgc cggaggaaac ggcagtcgcc tccccgcccg cgactgcatc cgtggagtcg   1260

tcgccactcc ccgccgcggc ggcaacgccc ggggccgggc acacgaacac cagcagcgcc   1320

cccgcagcga aaacgccccc caccacacca gcccccacga cccccccgcc cacgtctacc   1380

cacgcgaccc cccgccccac gactccgggg ccccaaacaa cccctcccgg acccgcaacc   1440

ccgggtccgg tgggcgcctc cgccgcaccc acggccgatt ccccccctcac cgcctcgccc   1500

cccgctaccg cgccggggcc ctcggccgcc aacgtttcgg tcgccgcgac caccgccacg   1560

cccggaaccc ggggcaccgc ccgtaccccc ccaacggacc caaagacgca cccacacgga   1620

cccgcggacg ctccccccgg ctcgccagcc cccccacccc ccgaacatcg cggcggaccc   1680

gaggagtttg agggcgccgg ggacggcgaa ccccccgatg acgacgacag cgccaccggc   1740

ctcgccttcc gaactccgaa ccccaacaaa ccaccccccg cgcgccccgg gcccatccgc   1800

cccacgctcc cgccaggaat tcttgggccg ctcgccccca acacgcctcg ccccccccgcc   1860

caagctcccg ctaaggacat gccctcgggc cccacacccc aacacatccc cctgttctgg   1920

ttcctaacgg cctcccctgc tctagatatc ctctttatca tcagcaccac catccacacg   1980

gcggcgttcg tttgtctggt cgccttggca gcacaacttt ggcgcggccg ggcggggcgc   2040

aggcgatacg cgcacccgag cgtgcgttac gtatgtctgc cacccgagcg ggattag      2097
```

<210> SEQ ID NO 14
<211> LENGTH: 11
<212> TYPE: PRT
<213> ORGANISM: Artificial Sequence
<220> FEATURE:
<223> OTHER INFORMATION: Artificial Cationic Antimicrobial Peptide KLKL5KLK

<400> SEQUENCE: 14

```
Lys Leu Lys Leu Leu Leu Leu Leu Lys Leu Lys
1               5                   10
```

<210> SEQ ID NO 15
<211> LENGTH: 915
<212> TYPE: DNA
<213> ORGANISM: herpes simplex virus 2

<400> SEQUENCE: 15
gccttgaccg aggacgcgtc ctccgattcg cctacgtccg ctccggagaa gacgcccctc 60
cctgtgtcgg ccaccgccat ggcgccctca gtcgacccaa gcgcggaacc gaccgccccc 120
gcaaccacta ctccccccga cgagatggcc acacaagccg caacggtcgc cgttacgccg 180
gaggaaacgg cagtcgcctc cccgcccgcg actgcatccg tggagtcgtc gccactcccc 240
gccgcggcgg caacgcccgg ggccgggcac acgaacacca gcagcgcccc cgcagcgaaa 300
acgcccccca ccacaccagc ccccacgacc cccccgccca cgtctaccca cgcgaccccc 360
cgccccacga ctccggggcc ccaaacaacc cctcccggac ccgcaacccc gggtccggtg 420
ggcgcctccg ccgcacccac ggccgattcc cccctcaccg cctcgccccc cgctaccgcg 480
ccggggccct cggccgccaa cgtttcggtc gccgcgacca ccgccacgcc cggaacccgg 540
ggcaccgccc gtaccccccc aacggaccca aagacgcacc cacacggacc cgcggacgct 600
ccccccggct cgccagcccc cccacccccc gaacatcgcg gcggacccga ggagtttgag 660
ggcgccgggg acggcgaacc ccccgatgac gacgacagcg ccaccggcct cgccttccga 720
actccgaacc ccaacaaacc accccccgcg cgcccccgggc ccatccgccc cacgctcccg 780
ccaggaattc ttgggccgct cgcccccaac acgcctcgcc cccccgccca agctcccgct 840
aaggacatgc cctcgggccc cacaccccaa cacatccccc tgttctggtt cctaacggcc 900
tcccctgctc tagat 915

<210> SEQ ID NO 16
<211> LENGTH: 999
<212> TYPE: DNA
<213> ORGANISM: Artificial Sequence
<220> FEATURE:
<223> OTHER INFORMATION: EXCT0-mgG-2

<400> SEQUENCE: 16
gccttgaccg aggacgcgtc ctccgattcg cctacgtccg ctccggagaa gacgcccctc 60
cctgtgtcgg ccaccgccat ggcgccctca gtcgacccaa gcgcggaacc gaccgccccc 120
gcaaccacta ctccccccga cgagatggcc acacaagccg caacggtcgc cgttacgccg 180
gaggaaacgg cagtcgcctc cccgcccgcg actgcatccg tggagtcgtc gccactcccc 240
gccgcggcgg caacgcccgg ggccgggcac acgaacacca gcagcgcccc cgcagcgaaa 300
acgcccccca ccacaccagc ccccacgacc cccccgccca cgtctaccca cgcgaccccc 360
cgccccacga ctccggggcc ccaaacaacc cctcccggac ccgcaacccc gggtccggtg 420
ggcgcctccg ccgcacccac ggccgattcc cccctcaccg cctcgccccc cgctaccgcg 480
ccggggccct cggccgccaa cgtttcggtc gccgcgacca ccgccacgcc cggaacccgg 540
ggcaccgccc gtaccccccc aacggaccca aagacgcacc cacacggacc cgcggacgct 600
ccccccggct cgccagcccc cccacccccc gaacatcgcg gcggacccga ggagtttgag 660
ggcgccgggg acggcgaacc ccccgatgac gacgacagcg ccaccggcct cgccttccga 720
actccgaacc ccaacaaacc accccccgcg cgcccccgggc ccatccgccc cacgctcccg 780
ccaggaattc ttgggccgct cgcccccaac acgcctcgcc cccccgccca agctcccgct 840
aaggacatgc cctcgggccc cacaccccaa cacatccccc tgttctggtt cctaacggcc 900
tcccctgctc tagatgcaca actttggcgc ggccgggcgg ggcgcaggcg atacgcgcac 960
ccgagcgtgc gttacgtatg tctgccaccc gagcgggat 999

<210> SEQ ID NO 17
<211> LENGTH: 1011
<212> TYPE: DNA
<213> ORGANISM: Artificial Sequence
<220> FEATURE:
<223> OTHER INFORMATION: EXCT4-mgG-2

<400> SEQUENCE: 17
gccttgaccg aggacgcgtc ctccgattcg cctacgtccg ctccggagaa gacgcccctc 60
cctgtgtcgg ccaccgccat ggcgccctca gtcgacccaa gcgcggaacc gaccgccccc 120
gcaaccacta ctccccccga cgagatggcc acacaagccg caacggtcgc cgttacgccg 180
gaggaaacgg cagtcgcctc cccgcccgcg actgcatccg tggagtcgtc gccactcccc 240
gccgcggcgg caacgccccgg ggccgggcac acgaacacca gcagcgcccc cgcagcgaaa 300
acgcccccca ccacaccagc cccacgacc ccccgccca cgtctaccca cgcgaccccc 360
cgccccacga ctccggggcc ccaaacaacc cctcccggac ccgcaacccc gggtccggtg 420
ggcgcctccg ccgcacccac ggccgattcc cccctcaccg cctcgccccc cgctaccgcg 480
ccggggccct cggccgccaa cgtttcggtc gccgcgacca ccgccacgcc cggaacccgg 540
ggcaccgccc gtacccccc aacggaccca aagacgcacc cacacggacc cgcggacgct 600
ccccccggct cgccagcccc cccaccccc gaacatcgcg gcggacccga ggagtttgag 660
ggcgccgggg acggcgaacc ccccgatgac gacgacagcg ccaccggcct cgccttccga 720
actccgaacc ccaacaaacc accccccgcg cgcccgggc ccatccgccc cacgctcccg 780
ccaggaattc ttgggccgct cgcccccaac acgcctcgcc cccccgccca agctcccgct 840
aaggacatgc cctcgggccc cacaccccaa cacatccccc tgttctggtt cctaacggcc 900
tcccctgctc tagatgtcgc cttggcagca caactttggc gcggccgggc ggggcgcagg 960
cgatacgcgc acccgagcgt gcgttacgta tgtctgccac ccgagcggga t 1011

<210> SEQ ID NO 18
<211> LENGTH: 20
<212> TYPE: DNA
<213> ORGANISM: Artificial Sequence
<220> FEATURE:
<223> OTHER INFORMATION: CpG Motif-Containing Adjuvant

<400> SEQUENCE: 18
tccatgacgt tcctgacgtt 20

<210> SEQ ID NO 19
<211> LENGTH: 128
<212> TYPE: PRT
<213> ORGANISM: Artificial Sequence
<220> FEATURE:
<223> OTHER INFORMATION: Peptide-mgG-2

<400> SEQUENCE: 19

Ala Pro Pro Pro Pro Glu His Arg Gly Gly Pro Glu Glu Phe Glu Gly
1 5 10 15

Ala Gly Asp Gly Glu Pro Pro Asp Asp Asp Asp Ser Ala Thr Gly Leu
20 25 30

-continued

```
Ala Phe Arg Thr Pro Asn Pro Asn Lys Pro Pro Pro Ala Arg Pro Gly
        35                  40                  45

Pro Ile Arg Pro Thr Leu Pro Pro Gly Ile Leu Gly Pro Leu Ala Pro
    50                  55                  60

Asn Thr Pro Arg Pro Pro Ala Gln Ala Pro Ala Lys Asp Met Pro Ser
65                  70                  75                  80

Gly Pro Thr Pro Gln His Ile Pro Leu Phe Trp Phe Leu Thr Ala Ser
                85                  90                  95

Pro Ala Leu Asp Ala Gln Leu Trp Arg Gly Arg Ala Gly Arg Arg Arg
            100                 105                 110

Tyr Ala His Pro Ser Val Arg Tyr Val Cys Leu Pro Pro Glu Arg Asp
        115                 120                 125
```

TRUNCATED GLYCOPROTEIN G OF HERPES SIMPLEX VIRUS 2

CROSS-REFERENCE TO RELATED APPLICATION(S)

This application is a National Phase Patent Application of International Patent Application Number PCT/EP2017/052070, filed on Jan. 31, 2017, which claims priority of Swedish Patent Application 1650122-3, filed Feb. 1, 2016. The entire contents of both of which are incorporated herein by reference.

SEQUENCE LISTING

The instant application contains a Sequence Listing which was previously submitted in ASCII format to WIPO and is hereby incorporated by reference in its entirety. Said ASCII copy filed in the International Patent Application Number PCT/EP2017/052070, was last modified on Jan. 31, 2017, and is named SeqListing.txt and is 27,889 bytes in size.

FIELD OF THE INVENTION

The present invention is directed to a novel protein comprising a truncated version of the mature glycoprotein G of herpes simplex virus 2 (HSV-2), a vaccine comprising said protein, and use thereof in therapy and as a diagnostic antigen for detection of HSV-2 infections.

BACKGROUND OF THE INVENTION

It is known that herpes simplex virus 2 (HSV-2) infects the genital mucosa and establishes a life-long infection in sensory ganglia. After a primary infection, HSV-2 may reactivate frequently, giving widespread genital lesions with considerable physical and psychological stress. A recent global estimate of HSV-2 infection concluded that 417 million people aged 15-49 years were infected in 2012, giving a world-wide prevalence of 11.3%. 19.2 million individuals were newly-infected 2012 (Looker, K. J., et al. 2015, PLoS One vol. 10, e114989). Furthermore, in newborns and in immunocompromised patients, HSV-2 infection can elicit severe and often fatal central nervous system infections.

As HSV-2 is the most common cause of genital ulcers globally, a major problem is that the infection strongly facilitates transmission of HIV. HSV-2 infection is associated with a three-fold increased risk of HIV acquisition among both men and women, implying that in areas of high HSV-2 prevalence a high proportion of HIV is attributable to HSV-2. This observation can be explained by the fact that local HSV-2 infection increases the number of HIV target cells, i.e. cervical CD4+ T-cells, in the genital mucosa. Furthermore, HSV-2 suppressive therapy with acyclovir reduced plasma HIV-1 RNA by 70% in dually infected women. The inventor concludes that an effective method for control of genital HSV-2 infection is of major public health importance. An efficacious vaccine will not only reduce genital lesions and other clinical manifestations of HSV-2 infection, but also reduce the risk of acquisition and transmission of HIV.

Human vaccine trials have been performed using HSV-2 glycoprotein B (gB-2) and/or glycoprotein D (gD-2) as antigens. The rationale has been that these proteins are essential for replication of HSV-2 and induce strong neutralizing antibody and T-cell responses in mice and humans.

Despite these promising background data, results from randomized double-blind placebo-controlled multicenter trials have been unexpectedly discouraging. A gB-2- and gD-2-based vaccine was tested on 2,400 subjects and yielded only transient protection against infection (Corey et al., JAMA, 1999, vol. 282, 331-40). A prophylactic clinical study, including HSV-1 seronegative women (in total 8,323 subjects), was conducted between 2002 and 2010 in the U.S. and Canada. However, the results from this study revealed that the vaccine failed to prevent HSV-2 infection or disease (Belshe et al., 2012, N Engl J Med vol. 366, 34). These results clearly indicate a failure of previous vaccine strategies.

HSV-1 and HSV-2 are closely related viruses with an overall proteome amino acid sequence identity of >80%. The HSV-1 and HSV-2 envelope glycoproteins are strong inducers of the human antibody response. The high degree of similarity between these viruses implies that the envelope proteins, with the exception of glycoprotein G, contain several identical immunogenic regions and, therefore, elicit cross-reactive B- and T-cell responses. In other words, the immune responses elicited from an HSV-1 infection also recognise HSV-2-related antigens and vice versa. However, it seems clear that cross-reactive immune responses after an HSV-1 infection do not suffice to induce protective immunity against HSV-2 infection. This statement is based on the observation that a previous HSV-1 infection does not confer protection against acquisition of HSV-2. This notion makes sense from an evolutionary point of view, in that HSV-2 is mostly sexually transmitted, and usually infects persons at an older age than does HSV-1. Thus, HSV-2 has evolved to escape cross-reactive B- and T-cell responses induced by most of the HSV-1 glycoproteins. Therefore, the lack of protective properties of immune responses to cross-reactive proteins may explain both the failure of using the cross-reactive gB and gD proteins as vaccines, and why a prior HSV-1 infection is not protective for HSV-2 transmission.

The present invention is directed towards antigens of HSV-2 glycoprotein G (gG-2), and their use in vaccines and therapy, such as vaccines and therapy to prevent HSV-2 infection, and as antigens for use in the detection of anti-HSV-2 antibodies.

The gG-2 protein is a protein encoded by the US4 gene, which, in HSV-2 strain 333, comprises 2097 nucleotides including the stop codon. The US4 gene of HSV-2 strain 333 has the GenBank accession number EU018098.1, and its encoded amino acid sequence (i.e. the HSV-2 strain 333 gG-2 amino acid sequence) is presented herein as SEQ ID NO: 1. The nucleotide sequence of the complete HSV-2 strain 333 US4 gene is presented in SEQ ID NO: 13. The gG-2 protein is unique among the HSV proteins in that gG-2 is cleaved into one amino terminal secreted moiety (sgG-2), and one carboxy terminal intermediate, which includes a transmembrane region. The carboxy terminal intermediate is further processed to form mature, membrane-bound gG-2 (mgG-2), as described in detail below. SEQ ID NO: 2 shows the amino acid sequence of the mgG-2 protein of strain 333, consisting of 354 amino acids corresponding to amino acids 345-698 of SEQ ID NO:1.

It is known from the prior art (Liljeqvist et al., 1998, J Gen Virol., vol. 79, 1215; Marsden et al., 1998, J Med Virol., vol. 56, 79; Grabowska et al., 1999, J Gen Virol., vol. 80, 1789; Levi et al., 1996, Clin and Diagn. Lab Immunol., vol. 3, 265; Tunbäck, P. et al., 2000, J Gen Virol., vol. 81, 1033; Tunbäck, P. et al., 2005, J Gen Virol., vol. 86, 247) that the immunodominant antibody-binding regions of gG-1 (HSV-1 glycoprotein G) and mgG-2 are localized in the homologous regions of the proteins and not in the unique regions, see FIG. 3A-B. Despite the fact that some of these regions have high similarity between the two proteins, no cross-reactivity has been shown between human anti-gG-1 and anti-mgG-2 antibodies.

U.S. Pat. No. 5,665,537 claims that the unique region of gG-2 has desirable type-specific properties, and that antibodies which bind this region can be used for HSV serotyping. The document notes that antibody-binding regions are also localised in the homologous regions of gG-1 and mgG-2, and states that antibodies which bind these regions are cross-reactive with the two proteins.

In WO 98/003543 it is claimed that the antibody-binding region of human anti-mgG-2 antibodies, encompassing the 38 amino acids illustrated in FIG. 3D, is type-specific, and that this protein can be used for prophylactic, therapeutic and diagnostic uses relating to HSV-2 infection. However, this prior art document states that only the antibody-binding region of mgG-2 is important.

In WO 96/17938 glycoprotein D and G of HSV-2 and glycoprotein E of HSV-1 are used for vaccine purposes. It is disclosed that mgG-2 should be produced without both the transmembrane and the intracellular region.

WO 2010/135747 relates to proteins for use in a therapeutic and/or prophylactic HSV-2 vaccine. The application focuses on gD-2 and ICP-4, and presents limited data related to gG-2. Although GenBank accession number NP_044534.1 refers to entire gG-2 (Table 2, page 12) the protein specified in SEQ ID 38 (page 82) includes only sgG-2. Nothing is stated about the fact that gG-2 is cleaved into two proteins with different biochemical properties, i.e. sgG-2 and mgG-2. This document is completely silent in relation to mgG-2.

Görander, S. et al. disclose in Viruses, 2014, vol. 6, pages 4358-4372 (*Anti-Glycoprotein G Antibodies of Herpes Simplex Virus* 2 *Contribute to Complete Protection after Vaccination in Mice and Induce Antibody-Dependent Cellular Cytotoxicity and Complement-Mediated Cytolysis*), that anti-mgG-2 antibodies, elicited after vaccination of mice with full length mgG-2 and adjuvant, are important for the outcome after genital challenge with HSV-2.

Levi et al. disclose in Clinical and Diagnostic Laboratory Immunology, 1996, vol. 3, pages 265-269 (*Peptide Sequences of Glycoprotein G*-2 *Discriminate between Herpes Simplex Virus Type* 2 (*HSV*-2) *and HSV*-1 *Antibodies*), that synthetic glycoprotein G peptides may be useful for HSV-2 serology based on peptides, or combinations of peptides and antigens.

WO 97/05488, of Chiron Corporation, discloses a method of detecting and diagnosing herpes simplex virus (HSV) infection.

In view of shortcomings with vaccines against HSV-2 infections tested so far, there is a medical need for a new vaccine strategy, with efficacy against HSV-2 infections, or diseases related thereto.

SUMMARY OF THE INVENTION

An aspect of the present invention is a protein comprising a truncated version of the HSV-2 protein mgG-2, said protein comprising:

(i) an extracellular region of mgG-2 (EX-mgG-2), or a truncated version thereof, of at least 285 amino acids; said extra cellular region or truncated version thereof having at least 90%, 95%, 96%, 97%, 98% or 99% sequence identity (% SI) to a peptide fragment of the corresponding length present in SEQ ID NO: 3;

(ii) a truncated transmembrane region of mgG-2 (t-TMR-mgG-2) of 2 to 15 amino acids; said truncated transmembrane region having at least 90%, 95%, 96%, 97%, 98% or 99% sequence identity (% SI) to a peptide fragment of the corresponding length present in SEQ ID NO: 6; and (iii) an intracellular region of mgG-2 (IC-mgG-2), or a truncated version thereof, of at least 18 amino acids; said intracellular region or truncated version thereof having at least 90%, 95%, 96%, 97%, 98% or 99% sequence identity (% SI) to a peptide fragment of the corresponding length present in SEQ ID NO: 8.

As described in more detail below, SEQ ID NO: 3 represents the extracellular region of the mgG-2 protein of HSV-2 strain 333, consisting of 305 amino acids corresponding to amino acids 345-649 of SEQ ID NO: 1; SEQ ID NO: 6 represents the transmembrane region of the mgG-2 protein of HSV-2 strain 333, consisting of 21 amino acids corresponding to amino acids 650-670 of SEQ ID NO: 1; and SEQ ID NO: 8 represents the intracellular region of the mgG-2 protein of HSV-2 strain 333, consisting of 28 amino acids corresponding to amino acids 671-698 of SEQ ID NO: 1

It will be understood that the three regions (i), (ii) and (iii) are linked together to form the truncated mgG-2 protein. In particular, the three regions may be linked together directly (i.e. the respective amino acid sequences of the regions are adjacent to one another in the truncated mgG-2 protein). More particularly, the three regions are linked together in the order (i)-(ii)-(iii), N-terminal to C-terminal. It is not however precluded that the order is reversed.

A protein of the invention may include extracellular and intracellular regions which have at least 90% (or more, as indicated above) sequence identity to the respective sequences as set out in SEQ ID NOs: 3 and 8 respectively (i.e. to the full length of the sequences of SEQ ID NOs:3 and 8). However, the invention is not limited to this and includes proteins with extra- and intracellular regions which are truncated and which hence may be defined with respect to parts (or portions, or sub-sequences) of the full-length sequences shown in SEQ ID NOs: 3 and 8 respectively, referred to above and herein as "peptide fragments" present in the respective sequences (i.e. the % SI may refer to a part of SEQ ID NOs 3 or 8, etc.). The transmembrane region is truncated relative to the full length transmembrane region and hence the % SI refers to sequence identity to a part of the sequence of SEQ ID NO.6. Various such parts (i.e. peptide fragments) of SEQ ID NOs 3, 6 and 8 are discussed further below.

The protein may be provided in the form of a fusion protein comprising the truncated mgG-2 protein of the invention, linked (or fused) to an amino acid sequence (that is to another amino acid sequence, i.e. an amino acid sequence which is not the truncated mgG-2 protein, or which is not derived from the mgG-2 or gG-2 protein). The other amino acid sequence may be linked to the truncated mgG-2 protein at one or both ends (i.e. at either the N-terminal or C-terminal end, or both). It may for example be a fusion partner which aids production or purification (e.g. a His-tag or any other affinity binding partner) or an amino acid sequence which has adjuvant function, or any other desired activity or property. For example the fusion partner may stabilise the protein, improve pharmacokinetics (e.g. increase half-life in the circulation) or enhance immunogenicity or function of the protein in any way. In an embodiment the truncated mgG-2 protein may be operatively linked/fused to an amino acid sequence. By operatively linked is meant that the amino acid sequences are linked such that the protein is able to perform its function (i.e. retains its activity). More particularly the linked/fused protein is able to function as a vaccine antigen or diagnostic antigen, e.g. as described herein.

A further aspect of the present invention is a pharmaceutical composition, such as a pharmaceutical vaccine composition, comprising a protein as herein described and claimed, and one or more components selected from the group consisting of adjuvant, stabilizer, buffer, surfactant, salt and/or preservative, as well as the use of such a pharmaceutical (vaccine) composition in the prevention and/or treatment of an HSV-2 related disease and/or infection.

An aspect of the present invention is a protein as herein described and claimed, for use in the prevention and/or treatment of an HSV-2 related disease and/or infection.

Also an aspect of the present invention is a protein as herein described and claimed, for use as a diagnostic antigen for the detection of HSV-2 specific antibodies.

According to this aspect, also provided is use of a protein as herein described and claimed as an antigen for the detection of HSV-2 specific antibodies.

Also provided is a method of detecting a HSV-2 specific antibody in a sample, said method comprising contacting a sample containing or suspected of containing a said antibody (e.g. a serum sample, or other clinical sample, or any other sample) with a protein as herein described and claimed, and detecting binding of an antibody to said protein.

An aspect of the present invention is an isolated nucleic acid encoding a protein as herein described and claimed.

An aspect of the present invention is a vector comprising a nucleic acid encoding a protein as herein described and claimed.

An aspect of the present invention is a cell comprising a vector as herein described and claimed.

An aspect of the present invention is a method for producing an HSV-2 vaccine, comprising the steps of transfecting a host cell with an expression vector (e.g. a plasmid) containing a truncated gene from HSV-2 (i.e. an expression vector comprising a nucleotide molecule comprising a nucleotide sequence) encoding a protein as herein described and claimed.

The term "protein" is used herein synonymously and interchangeably with the term "polypeptide", and thus the term includes proteins, polypeptides and peptides.

DESCRIPTION OF THE INVENTION

I. The Biochemical Properties of mgG-2

An embodiment of the present invention is to use a truncated version of the membrane-bound portion (mgG-2) of glycoprotein G (gG-2) of herpes simplex virus 2 to induce an immune response.

Figure 1:
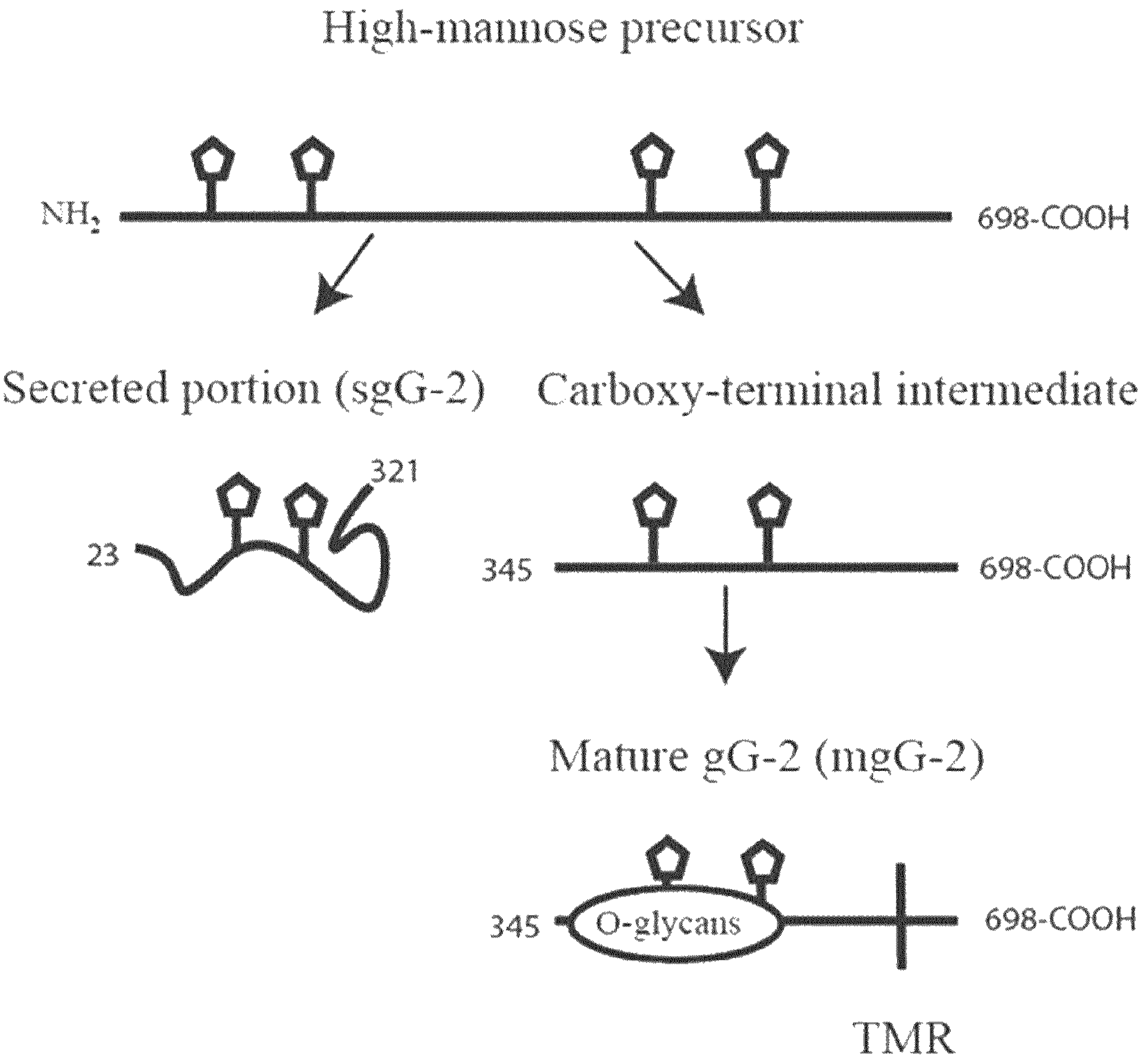
FIG. 1 is an illustration of the processing of the gG-2 protein. TMR represents the transmembrane region. The amino acid designation is based on HSV-2 strain 333 with the accession number EU018098.1. Lollipops represent N-glycans.

The proposed processing of the gG-2 protein into sgG-2 and mgG-2 is illustrated in FIG. 1. As shown therein, the N-glycosylated, high-mannose precursor gG-2 is cleaved into sgG-2 and a carboxy terminal high-mannose intermediate protein that is further processed by O-glycosylation to form the mature or membrane bound gG-2 (mgG-2). In addition, mgG-2 is processed by the trimming of the high-mannose N-linked glycans, and addition of further sugar residues generating N-linked glycans of the complex type. Two N-glycans were identified on each cleavage product. Most of the gain in molecular mass of the carboxy terminal intermediate (MW 74-77 kDa) when processed to form the mature mgG-2 (MW 112-120 kDa) is proposed to be due to extensive O-glycosylation.

The normal gG-2 cleavage-processing pathway is not dependent on the presence of other HSV-2 gene products. Instead, the cleavage event is proposed to be mediated by a host cell-specific protease. In recombinantly produced carboxy terminal-truncated mgG-2 in baculovirus-infected insect cells, the N-terminal amino acid of mgG-2 is alanine, equivalent to Ala345 of the precursor protein as shown in SEQ ID NO: 1 (WO 97/05488).

The inventor has shown by amino acid sequencing that the cleavage site of HSV-2 strain 333 gG-2 is identical in mammalian CHO cells, i.e. it is located between Met344 and Ala345 of SEQ ID NO: 1. This can be seen in SEQ ID NOs: 3-5. The amino acid sequence of strain 333 mgG-2 is presented in SEQ ID NO: 2.

Unlike N-glycosylation, which involves an asparagine residue in the sequence Asn-Xaa-Thr/Ser (Xaa can be any amino acid except proline), no particular sequence motif has been described for O-glycosylation. The O-glycosidic link of the sugar residue N-acetylgalactosamine to the amino acid serine or threonine (known as the Tn-antigen) is often referred to as mucin-type O-glycosylation. Clusters of these sugars have affinity to *Helix pomatia* agglutinin (HPA) lectin, which was used for purification of entire native mgG-2.

The mgG-2 protein is about 354 amino acids long and contains two occupied N-glycosylation sites, to which complex N-glycans are attached. The two N-glycosylation sites are located at amino acid positions 436-438 and 511-513 (the mgG-2 amino acid sequence is numbered such that each amino acid has the same number as it does in the gG-2 precursor, i.e. the first residue of mgG-2 is annotated as Ala345). Specifically, mgG-2 is N-glycosylated on Asn436 and Asn511. In addition, the mgG-2 protein contains 74 serine or threonine residues, amino acids which are potentially targets for O-glycosylation, mostly clustered at the amino-terminus of mgG-2.

As mentioned above, the mgG-2 protein is a transmembrane protein. It has an extracellular N-terminal domain and an intracellular C-terminal domain. The extracellular domain runs from Ala345 to about Asp649, based on which it is defined herein as having the sequence set forth in SEQ ID NO: 3 or a sequence having at least 90% sequence identity thereto. The transmembrane domain runs from about Ile650 to Ala670, based on which it is defined herein as having the sequence set forth in SEQ ID NO: 6 or a sequence having at least 90% sequence identity thereto. The intracellular domain runs from about Ala671 to Asp698, based on which it is defined herein as having the sequence set forth in SEQ ID NO: 8 or a sequence having at least 90% sequence identity thereto. As described in more detail below, the mgG-2 protein may vary both in length and amino acid sequence between different strains and isolates of HSV-2, and hence the lengths and amino acid sequences of the extracellular, transmembrane and intracellular domains (regions) may not be exactly as set out in SEQ ID NOs: 3, 6 or 8, and may vary therefrom.

II. mgG-2 as an Antigen for Detection of Type-Specific HSV-2 Antibodies

Serological assays which can detect HSV-2 type-specific antibodies are important for example in the estimation of seroprevalences in epidemiological studies, for detecting subjects infected with HSV-2, for counselling patients and for discrimination between primary and recurrent HSV-2 infection. The gG-1 of HSV-1 and mgG-2 of HSV-2 have been shown to elicit exclusively type-specific antibody responses (i.e. gG-1 elicits an antibody response exclusively specific for gG-1 and mgG-2 elicits an antibody response exclusively specific for mgG-2).

Figure 3:
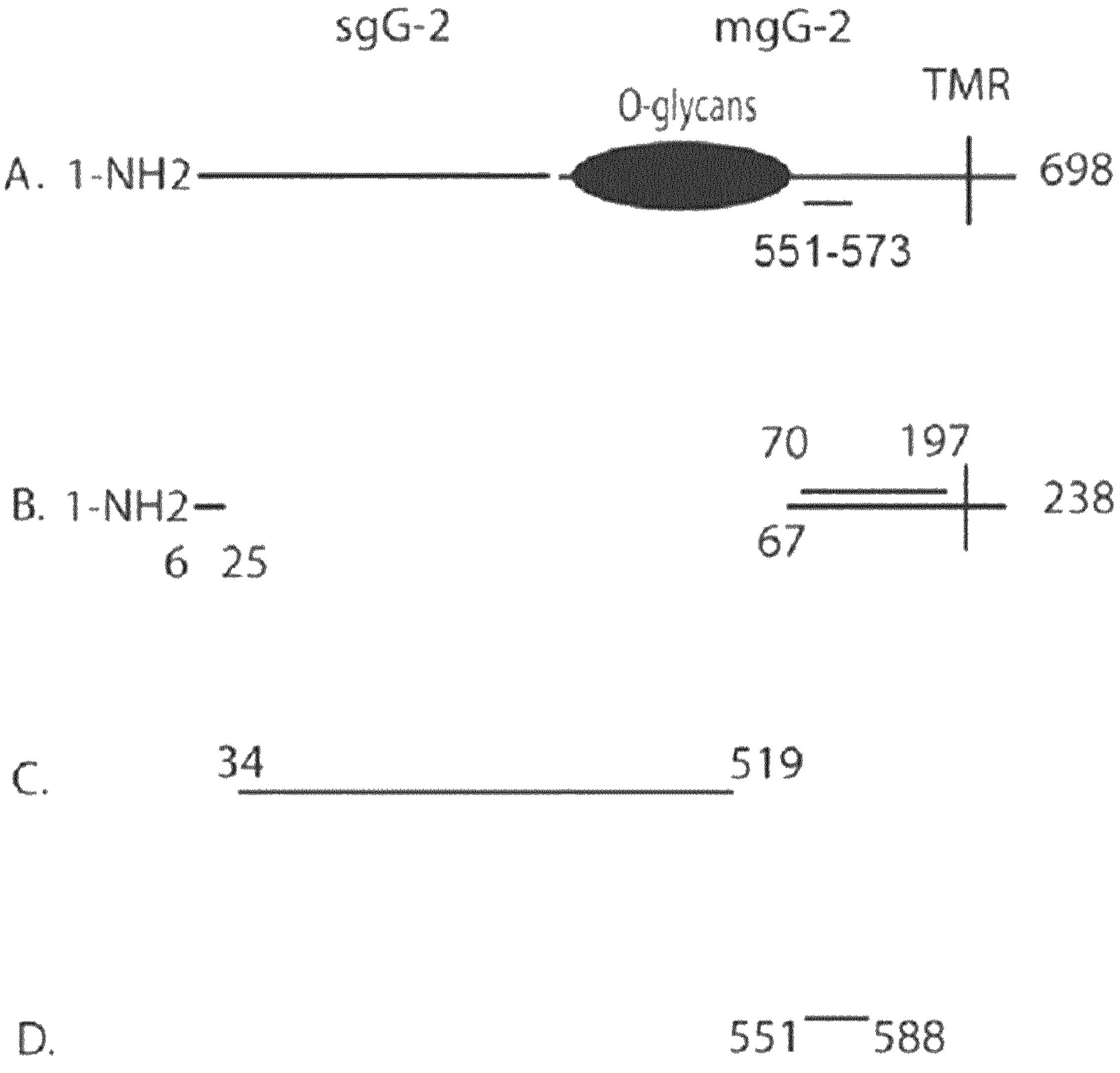
FIGS. 3A-D are schematic presentations of mgG-2 of HSV-2 (strain 333 with accession number EU018098.1.). A. The immunodominant region to which human antibodies bind (amino acids 551-573) is marked. The transmembrane region of mgG-2 is marked as TMR. B. Schematic presentation of the gG-1 protein (from HSV-1 strain 17; accession number X14112). gG-1 amino acids 6-25 and 67-238 represent the homologous regions containing >45% identical amino acids with gG-2. Most of sgG-2 and the O-glycan-rich region of mgG-2 are unique to gG-2, i.e. corresponding residues in gG-1 are lacking. The immunodominant region to which human antibodies bind to gG-1 (amino acids 70-197) is marked. The transmembrane region of gG-1 is marked with a vertical line. C. The unique region of gG-2 described in U.S. Pat. No. 5,665,537. D. Antibody-binding region of 38 amino acids described in WO 98/003543.

The inventor and others have shown (Liljeqvist et al., 1998, J Gen Virol., vol. 79., 1215; Marsden et al., 1998, J Med Virol., vol. 56, 79; Grabowska et al., 1999, J Gen Virol., vol. 80, 1789; Levi et al., 1996, Clin and Diagn. Lab Immunol., vol. 3, 265; Tunbäck et al., 2000, J Gen Virol., vol 81, 1033; Tunbäck et al. 2005, J Gen Virol., vol. 86, 247) that the immunodominant antibody-binding regions of gG-1 and mgG-2 are localized in the regions which are homologous (so-called "homologous regions") between the proteins, and not in the unique regions (see FIG. 3A-B), and despite the fact that some of the regions of the two proteins have high similarity, no cross-reactivity has been shown between human anti-gG-1 and anti-mgG-2 antibodies. The inventor has shown that the type-specific recognition of gG-1 or mgG-2 by human anti-gG-1 and anti-mgG-2 antibodies, respectively, is the result of binding to epitopes containing single or double (i.e. neighbouring) type-specific amino acids (Tunbäck et al., 2005, J Gen Virol., vol. 86, 247). Thus, the epitopes recognised by anti-gG-1 and anti-mgG-2 antibodies are not present in mgG-2 or gG-1, respectively. The inventor concludes that in contrast to what is stated in U.S. Pat. No. 5,665,537, the antibody-binding regions of gG-1 and mgG-2 are mostly localized in the homologous regions. Thus, despite the high sequence similarity between the proteins, no cross-reactivity of antibodies is detected.

Native mgG-2 including the entire extracellular (EX) region, entire transmembrane region (TMR) and entire intracellular (IC) region, derived from virus-infected cells, has been used for several years as type-specific antigen in serodiagnosis of HSV-2 infection in different formats such as ELISA, immunodot and Western blot. Expression of full length gG-2 in different recombinant systems such as *E. coli* or baculovirus expression systems has also been described. Furthermore, Boucher et al. (Clin Diagn Virol, 1993, vol. 1, 29) expressed the entire gG-2 protein in CHO cells, including the TMR and the IC domain minus the eight most carboxy terminal-located amino acids, and used this protein for detection of human anti-gG-2 antibodies.

The expression of gG-2 in recombinant systems is achieved by well-known techniques to simplify the production and purification process, often by deleting the transmembrane region which will facilitate the secretion of the target protein. In several studies different truncated mgG-2 proteins have been expressed in *E. coli*, yeast or insect cells.

Using peptides derived from the mgG-2 sequence, immunoreactive regions have been defined. In a report from 1996 (Clin and Diagn Lab Immunol, vol. 3, 265), Levi et al. identified three type-specific mgG-2 peptides which were reactive with anti-mgG-2 antibodies. Two of the seroreactive peptides were located in the middle (peptide G2-69) and the carboxy terminal part (peptide G2-70) of the intracellular region. The peptide covering the carboxy terminal part of the TMR and the junction between the TMR and the amino terminal part of the intracellular region presented low reactivity (peptide G2-68). Similar results were presented by Grabowska el al. (J Gen Virol 1999, vol. 80, 1789). Thus, the region covered by peptide G2-68 was of minor importance to elicit an anti-mgG-2 antibody response.

Staffan Görander and the inventor have shown that HPA-lectin purified native mgG-2 (full length mgG-2) antigen in an ELISA format presents significantly higher specificity of identification of HSV-2-specific antibodies among blood donors from an African population as compared with the commercially-available HerpeSelect2 (Focus Diagnostics Inc., Cypress, US). We also suggested in 2010 (Thesis, Functions of glycoprotein G of herpes simplex virus type 2, ISBN 978-91-628-8005-7) "that the mgG-2 and/or sgG-2 antigens produced in CHO-cells have the potential to be the best ELISA antigen for detection of HSV-2 specific antibodies".

An ideal antigen for detection of specific HSV-2 antibodies, used as a marker of HSV-2 infection, will present 100% sensitivity, i.e. all HSV-2 infected individuals are correctly identified, and 100% specificity, i.e. all individuals not infected with HSV-2 are correctly identified. No such assays or antigens are available. One reason for these shortcomings is the selection of the antigen and how the antigen is produced. In an ELISA format, using well-defined cohorts of serum samples, the inventor compared the performance (sensitivity and specificity) of three antigens: i) the truncated version of mgG-2 produced in CHO cells (EXCT4-mgG-2, FIG. 2D), ii) HPA-lectin purified native mgG-2 (HPA-mgG-2, FIG. 2A), and iii) a 128 amino acid-long synthetic peptide covering the immunodominant regions located in both the extracellular and the intracellular regions of mgG-2, (Example 5, Table 1). From these data the inventor concludes that both EXCT4-mgG-2 and HPA-mgG-2 present higher specificity among HSV-1-infected individuals than the 128 amino acid-long synthetic peptide, and most importantly, that the EXCT4-mgG-2 presented higher specificity than both HPA-mgG-2 and the 128 amino acid-long synthetic peptide among selected HSV-2-negative blood donors in Tanzania. These samples were earlier classified as false positive using HerpeSelect2. It was surprising that EXCT4-mgG-2 presented higher specificity than HPA-mgG-2, which has been shown to present higher specificity than the FDA-approved HerpeSelect2, (Görander, et al., 2006, Clin. Vaccine Immunol. vol. 13, 633).

Thus, the protein may be used to specifically or selectively detect antibodies which are specific to HSV-2, e.g. to selectively detect or discriminate such antibodies from HSV-1 antibodies. As noted above, this has particular utility clinically or epidemiologically (i.e. to detect or determine a HSV-2 infection in a subject), but this aspect of the invention is not limited to such use, and includes any use or method of detecting anti-HSV-2 antibodies in any sample, for example in research or laboratory use, or in the production of antibodies etc.

Accordingly, the sample in which the antibodies are detected may be any sample which may contain an antibody. This may be any clinical or biological sample, e.g. a cell culture or culture supernatant, as well as a cell, tissue or fluid sample from the body of a subject. Such a sample may typically be a blood or blood-derived sample, especially serum, plasma and such like, etc.

The detection may be carried out using methods well known and widely described in the art to detect the binding of antibody to an antigen (i.e. using any known immunoassay procedure, as appropriate). Thus, by way of example, an antibody bound to the antigen (i.e. the target, or test, antibody), may be detected using antibodies or other binding agents capable of binding to the target/test antibody, e.g. to the Fc part thereof. Such detecting antibodies/binding agents may be labelled or their binding to the target/test antibody may be detected by other means. The antigen, in this case the protein of the invention, may or may not be immobilised on a solid support. The assay format may thus be solid phase-based, e.g. sandwich assays, or it may be homogenous (not requiring a solid phase), e.g. a competitive assay format. For example, the assay method may be an ELISA.

III. mgG-2 as a Vaccine

The inventor has discovered that the entire mgG-2 protein produced from virus-infected mammalian cells and purified by HPA-lectin can be used as a vaccine, together with adjuvant, for protection from genital HSV-2 disease.

The state of the art for production of subunit vaccines is to use truncated proteins, i.e. proteins where the transmembrane region (TMR) and often the intracellular (IC)-region have been removed to facilitate the production process and secretion of the protein into the cell medium.

In one aspect of the invention, the present inventor has recombinantly produced three truncated versions of mgG-2 in mammalian cell lines.

The first truncated version is an mgG-2 protein consisting of only the extracellular region of mgG-2 and thereby lacking both the TMR and IC-region (EX-mgG-2; SEQ ID NO: 3 (305 amino acids). An aspect of the present invention is accordingly a truncated mgG-2 protein consisting of only the extracellular region of mgG-2, or a part thereof, and thereby lacking both the TMR and IC-region, e.g. a protein comprising SEQ ID NO.3 but no other sequence from mgG-2, or a protein consisting of SEQ ID NO.3.

The second truncated version is an mgG-2 protein consisting of the extracellular and intracellular regions but with no residues originating from the TMR (EXCT0-mgG-2; SEQ ID NO: 4 (337 amino acids). An aspect of the present invention is accordingly an mgG-2 protein consisting of the extracellular and intracellular regions, or parts thereof, but with no residues originating from the TMR, e.g. a protein comprising of consisting of SEQ ID NO.4. Such a protein can be produced in e.g. CHO and HEK293 cells.

The third truncated version is an mgG-2 protein consisting of the extracellular region, four amino acids of the carboxy terminal end of the TMR (residues VALA (SEQ ID NO: 7)) and the intracellular region (EXCT4-mgG-2; SEQ ID NO: 5). An aspect of the present invention is accordingly an mgG-2 protein comprising or consisting of the extracellular region or a part thereof, four amino acids of the carboxy terminal end of the TMR (residues VALA (SEQ ID NO: 7)) and the intracellular region or a part thereof. A protein comprising or consisting of SEQ ID NO. 5 represents an embodiment of this aspect of the invention.

In a vaccination model in mice, the inventor has shown that EX-mgG-2 produced in CHO cells resulted in a significantly lower survival rate and increased disease scores as compared with native full-length mgG-2 (HPA-mgG-2) and EXCT4-mgG-2 (p=0.0006, FIG. 4A). Furthermore, a combination of EXCT0-mgG-2 produced in CHO and in HEK293 cells resulted in a significantly lower survival rate and higher disease scores as compared with native full-length mgG-2 produced from virus-infected GMK-AH1 cells and EXCT4-mgG-2 produced in CHO cells. Both HPA-mgG-2 and EXCT4-mgG-2 induced complete protection with low disease scores.

It is clear from the vaccination data provided herein that the truncated versions of mgG-2 present different effects as a vaccine in the mouse genital model. EXCT4-mgG-2 was most effective and induced similar protection to full-length mgG-2.

It was notable, surprising and significantly important that the protein EXCT4-mgG-2 produced in CHO cells, when used as a vaccine in mice, as compared with full-length HPA-mgG-2 gives different and de novo antibody responses, similar reduction of infectious HSV-2 in the genital tract as well as local IFNγ response in vaginal washes after challenge with fully virulent HSV-2. Remarkably, EXCT4-mgG-2 induced a qualitatively different cellular response as immunization antigen. After vaccination with EXCT4-mgG-2 no significant proliferation or IFNγ production was detected from enriched spleen CD4+ T-cells.

Thus one aspect of the present invention is a recombinant protein EXCT4-mgG-2 (SEQ ID NO: 5), which encompasses amino acids 345-649 of the extracellular region of mgG-2 (SEQ ID NO: 3); amino acids 667-670 of the TMR of mgG-2 (SEQ ID NO: 7); and amino acids 671-698 of the intracellular region of mgG-2 (SEQ ID NO: 8). Thus, 17 amino acids of the TMR are deleted in EXCT4-mgG-2 (as seen from comparison of SEQ ID NO: 2 with SEQ ID NO: 5). The amino acid residue numbers are given with respect to SEQ ID NO:1, and represent the positions of the respective regions, or parts thereof, therein. As described elsewhere herein, a protein of the invention may comprise an amino acid sequence as set forth in SEQ ID NO: 5, or an amino acid sequence having at least 90% sequence identity therewith, e.g. the sequence may be comprised in a fusion protein.

However, the invention is not limited only to proteins having, or based on, the sequence of SEQ ID NO: 5, and includes other truncated mgG-2 proteins having other truncated TMR regions.

An aspect of the present invention is a protein comprising a truncated version of the HSV-2 protein mgG-2, said protein comprising:

(i) an extracellular region of mgG-2 (EX-mgG-2), or a truncated version thereof of at least 285 amino acids; said extracellular region or truncated version thereof having at least 90%, 95%, 96%, 97%, 98% or 99% sequence identity (% SI) to a peptide fragment of the corresponding length present in SEQ ID NO: 3;

(ii) a truncated transmembrane region of mgG-2 (t-TMR-mgG-2) of 2 to 15 amino acids; said truncated TMR having at least 90%, 95%, 96%, 97%, 98% or 99% sequence identity (% SI) to a peptide fragment of the corresponding length present in SEQ ID NO: 6; and (iii) an intracellular region of mgG-2 (IC-mgG-2), or a truncated version thereof of at least 18 amino acids; said intracellular region or truncated version thereof having at least 90%, 95%, 96%, 97%, 98% or 99% sequence identity (% SI) to a peptide fragment of the corresponding length present in SEQ ID NO: 8.

The deleted region of the TMR (i.e. that region of the TMR of native mgG-2 which is deleted to form the truncated TMR of 2-15 amino acids present in the mgG-2 proteins of the invention) may include from 6 to 19 amino acids (such that from 2 to 15 amino acids remain of the 21 present in the native TMR sequence). For example, 6, 7, 8, 9, 10, 11, 12, 13, 14, 15, 16, 17, 18, or 19 amino acids of the TMR can be deleted, as long as the resultant truncated mgG-2 protein is secreted and not retained inside the cell or in the cell membrane. Any of the 21 amino acids of the native TMR sequence can be deleted to form the truncated mgG-2 protein of the invention, though as mentioned above in certain embodiments the N-terminal 17 amino acids of the native TMR sequence are deleted, such that the C-terminal 4 amino acids (which have the sequence of SEQ ID NO: 7) remain. In some embodiments, some of the retained amino acids of the TMR can be modified or substituted, as long as the resultant protein is secreted and not retained inside the cell or in the cell membrane. Accordingly, in other words, the truncated TMR is not able to act as a transmembrane region and the truncated mgG-2 protein, when expressed in a cell, is not located in the membrane, nor retained in the cytoplasm, but is secreted. The truncated TMR is not able to localise the protein to the cell membrane.

According to an embodiment of the present invention, the truncated TMR comprises between (i.e. from) 2 to 10 amino acids (AA), such as between (i.e. from) 3 to 5 amino acids (AA).

In other embodiments the truncated TMR may comprise a part of the amino acid sequence as shown in SEQ ID NO: 6 (or of an amino acid sequence having at least 90% sequence identity thereto), wherein said part comprises 2-15, 2-14, 2-12, 2-10, 2-9, 2-8, 3-15, 3-14, 3-12, 3-10, 3-9, 3-8, 3-7, 3-6, 3-5, 4-15, 4-14, 4-12, 4-10, 4-9, 4-8, 4-7, 4-6, or 4-5 consecutive amino acid residues of SEQ ID NO: 6 (or of an amino acid sequence having at least 90% sequence identity thereto).

In one aspect of the present invention, the truncated TMR has at least 90%, such as at least 95%, 96%, 97%, 98% or 99%, sequence identity (% SI) to a peptide fragment of the corresponding length present in SEQ ID NO: 9. SEQ ID NO: 9 represents amino acids 1-10 of the full length TMR sequence as set out in SEQ ID NO: 6.

In an embodiment of the present invention, the truncated TMR has at least 90%, such as at least 95%, 96%, 97%, 98% or 99%, sequence identity (% SI) to a peptide fragment of the corresponding length present in SEQ ID NO: 10. SEQ ID NO: 10 represents amino acids 11-21 of the full length TMR sequence as set out in SEQ ID NO: 6.

In an embodiment of the present invention, the truncated TMR has at least 80%, such as at least 90%, 95%, 96%, 97%, 98% or 99%, sequence identity (% SI) to a peptide fragment of the corresponding length present in SEQ ID NO: 11. SEQ ID NO: 11 represents amino acids 1-5 of the full length TMR sequence as set out in SEQ ID NO: 6.

In an embodiment of the present invention, the truncated TMR has at least 80%, such as at least 90%, 95%, 96%, 97%, 98% or 99%, sequence identity (% SI) to a peptide fragment of the corresponding length present in SEQ ID NO: 12. SEQ ID NO: 12 represents amino acids 17-21 of the full length TMR sequence as set out in SEQ ID NO: 6.

In other embodiments, the protein of the invention may comprise a TMR which has an amino acid sequence as set forth in any one of SEQ ID NOs: 7 or 9-12, or an amino acid sequence which comprises 1-3, such as 1-2 or 1, amino acid deletions, additions and/or substitutions relative thereto.

The present invention provides an mgG-2 protein comprising a truncated TMR. As mentioned above, in native mgG-2 the TMR spans, following the sequence numbering of SEQ ID NO: 1, approximately amino acids residues 650-670 (while the extracellular region (EX) spans approximately amino acids residues 345-649, and the intracellular region (IC) spans approximately amino acids residues 671-698).

In an embodiment of the present invention, the truncated TMR (i.e. the region of the TMR which is retained following the deletion) comprises a portion of the TMR, for example at least 4 amino acids between residues 650-670. In the proteins of the present invention, a region of the TMR comprising between 6 and 19 amino acids is deleted relative to native mgG-2. Thus, the deletion may be between 6-18, 6-16, 6-15, 6-12, 6-10, 7-19, 7-18, 7-16, 7-15, 7-12, 7-10, 8-19, 8-18, 8-16, 8-15, 8-12, 8-10 residues long etc. (or indeed any range between the integers of 6 and 19), and may be from the C-terminal end, N-terminal end, and/or internal in the sequence of the TMR.

In an embodiment of the present invention, at least one residue in the TMR has been modified, deleted or substituted, and the produced protein is secreted and not retained inside the cell or in the cell membrane. For example, a variant may have its internal deletion begin at, following the sequence numbering of SEQ ID NO: 6 (which is the sequence of the mgG-2 TMR), amino acid residue 1, 2, 3, 4, 5, 6, 7, 8, 9, 10, 11, 12, 13, 14, 15 or 16, and end at amino acid residue 6, 7, 8, 9, 10, 11, 12, 13, 14, 15, 16, 17, 18, 19, 20, or 21.

In an embodiment of the present invention, the extracellular region of mgG-2 (EX-mgG-2) and/or the intracellular region of mgG-2 (IC-mgG-2) may be truncated.

In one embodiment of the present invention, a truncated extracellular region of mgG-2 (EX-mgG-2) may share at least 90%, such as at least 95%, 96%, 97%, 98% or 99%, sequence identity (% SI) to a peptide fragment of the corresponding length present in SEQ ID NO: 3.

In one embodiment of the present invention, a truncated extracellular region of mgG-2 (EX-mgG-2) may comprise at least 285, 290, 295, or 300 (out of 305) amino acids. Thus the extracellular region of mgG-2 comprised within the proteins of the present invention may be truncated by up to 20 amino acids, i.e. they may contain a deletion of up to 20 amino acids relative to the full-length sequence of the mgG-2 extracellular region (assuming the mgG-2 extracellular region used is that of HSV-2 strain 333 mgG-2, whose sequence is presented in SEQ ID NO: 3; if the extracellular region used is of a different mgG-2 of a different length (longer or shorter than 305 amino acids), commensurately more or fewer amino acids may be deleted from the wild-type sequence to yield the truncated sequence to be used in a protein of the invention). The deletion may be of up to 20 amino acids, e.g. 1, 2, 3, 4, 5, 6, 7, 8, 9, 10, 11, 12, 13, 14, 15 16, 17, 18, 19 or 20 amino acids.

The truncated extracellular region of mgG-2 in the proteins of the invention is preferably truncated at its N-terminus or its C-terminus (or both its N- and C-termini), such that the truncated extracellular region consists of at least 285 amino acids which are contiguous in the native sequence of the protein. In other words it is preferable that the deletion of the up to 20 amino acids from the extracellular region of mgG-2 is made from one or other end of the sequence. However, in some embodiments up to 20 amino acids may be deleted internally, from within the sequence of the extracellular domain of mgG-2 (i.e. the deletion need not include either the N- or C-terminal amino acids of the domain). Thus there is no limitation as to where the deletion may be made from.

As indicated, the truncation need not be of up to 20 contiguous amino acids: the truncation may be obtained by the deletion of up to a total of 20 amino acids from any number of locations (up to 20 locations) within the sequence of the mgG-2 extracellular region. For instance, two sequences of 10 (or up to 10) amino acids may be deleted from separate locations within the mgG-2 extracellular region (e.g. the 10 most N-terminal and the 10 most C-terminal amino acids could be deleted). Alternatively, 4 sequences of 5 (or up to 5) amino acids may be deleted from separate locations within the region, or any other similar selection of amino acid sequences of an appropriate length, so long as the truncated extracellular region is at least 285 amino acids in length. The truncated extracellular region has at least 90% amino acid identity to a contiguous amino acid sequence found within SEQ ID NO: 3 and of the same length as the truncated extracellular region.

Thus, a 285 amino acid-long truncated extracellular region must have at least 90% sequence identity to a contiguous sequence of 285 amino acids from within SEQ ID NO: 3. For instance, it could have at least 90% sequence identity to residues 1-285, 2-286, 3-387, 4-288, 5-289, 6-290. 7-291, 8-292, 9-293, 10-294, 11-295, 12-296, 13-297, 14-298, 15-299, 16-300, 17-301, 18-302, 19-303, 20-304 or 21-305 of SEQ ID NO: 3. Longer truncated extracellular regions must have at least 90% sequence identity to correspondingly longer contiguous amino acid sequences found within SEQ ID NO: 3, which can be similarly identified by the skilled person.

Preferably, the truncated extracellular region has at least 90% amino acid sequence to SEQ ID NO: 3. If the extracellular region has at least 285 amino acids, and aside from the up to 20 amino acid truncation no mutations are made to the truncated extracellular region, such an extracellular region falls within the scope of the invention.

In an embodiment of the invention, a truncated intracellular region of mgG-2 (IC-mgG-2) may share at least 90%, such as at least 95%, 96%, 97%, 98% or 99% sequence identity (% SI) to a peptide fragment of the corresponding length present in SEQ ID NO: 8.

In one embodiment of the invention, a truncated intracellular region of mgG-2 (IC-mgG-2) may comprise at least 18, 20, 22, 24, or 26 (out of 28) amino acids. Thus the intracellular region of mgG-2 comprised within the proteins of the present invention may be truncated by up to 10 amino acids, i.e. they may contain a deletion of up to 10 amino acids relative to the full-length sequence of the mgG-2 intracellular region (assuming the mgG-2 intracellular region used is that of HSV-2 strain 333 mgG-2, whose sequence is presented in SEQ ID NO: 8; if the intracellular region used is of a different mgG-2 of a different length (longer or shorter than 28 amino acids), commensurately more or fewer amino acids may be deleted from the wild-type sequence to yield the truncated sequence to be used in a protein of the invention). The deletion may be of up to 10 amino acids, e.g. 1, 2, 3, 4, 5, 6, 7, 8, 9 or 10 amino acids.

The truncated intracellular region of mgG-2 in the proteins of the invention is preferably truncated at its N-terminus or its C-terminus (or both its N- and C-termini), such that the truncated intracellular region consists of at least 18 amino acids which are contiguous in the native sequence of the protein. In other words it is preferable that the deletion of the up to 10 amino acids from the intracellular region of mgG-2 is made from one or other end of the sequence. The truncated intracellular region has at least 90% amino acid identity to a contiguous sequence of amino acids found within the full-length sequence of the mgG-2 intracellular region, presented in SEQ ID NO: 8 (preferably it has at least 90% sequence identity to the sequence of SEQ ID NO: 8). If the up to 10 amino acids are deleted from the N-terminus of the mgG-2 intracellular region, or from the C-terminus of the mgG-2 intracellular region, or from a combination of the N- and C-termini of the mgG-2 intracellular region (e.g. if 5 amino acids are deleted from the N-terminus and 5 amino acids from the C-terminus of the intracellular region) the resultant truncated intracellular region will consist of an amino acid sequence which is found within SEQ ID NO: 8. Thus the truncated intracellular region of the proteins of the present invention may be truncated at its termini by a total of up to 10 amino acids. Such a protein inherently falls within the scope of the invention.

However, in some embodiments at least 1 of the up to 10 amino acids deleted from the mgG-2 intracellular region may be deleted internally, from within the sequence of the intracellular domain of mgG-2 (i.e. the deletion need not include either the N- or C-terminal amino acids of the domain). Thus there is no limitation as to where the deletion may be made from. In this embodiment, the truncated intracellular region has at least 90% amino acid sequence identity to a contiguous amino acid sequence found within SEQ ID NO: 8 and of the same length as the truncated intracellular region of mgG-2. Thus, an 18 amino acid-long truncated intracellular region of mgG-2 must have at least 90% sequence identity to a contiguous sequence of 18 amino acids found within SEQ ID NO: 8. For instance, an 18 amino acid-long truncated intracellular region may have at least 90% sequence identity with amino acid residues 1-18, 2-19, 3-20, 4-21, 5-22, 6-23, 7-24, 8-25, 9-26, 10-27 or 11-28 of SEQ ID NO: 8. Longer truncated intracellular regions must have at least 90% sequence identity to correspondingly longer contiguous amino acid sequences found within SEQ ID NO: 8, which can be similarly identified by the skilled person.

In one embodiment, the protein of the invention has the amino acid sequence of SEQ ID NO: 5, or an amino acid sequence with at least 90%, 95%, 96%, 97%, 98% or 99% sequence identity (% SI) with SEQ ID NO: 5.

Figure 2:
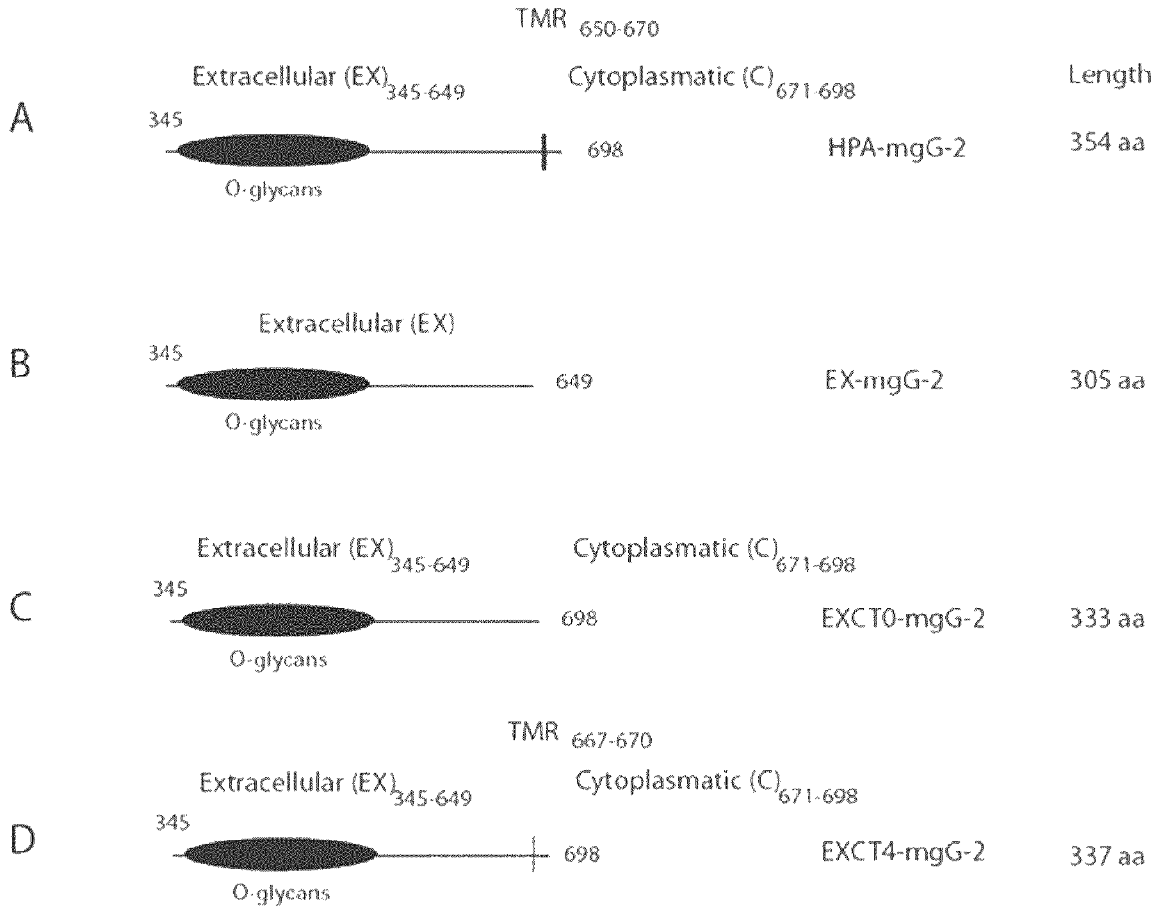
FIGS. 2A-D are schematic presentations of full-length and truncated versions of mgG-2 of HSV-2 strain 333 based on accession number EU018098.1. The cytoplasmic region is referred to elsewhere in the text as the intracellular region, the two terms being synonymous.

Further, the truncated TMR may contain exactly four amino acids, as in SEQ ID NO: 7 and depicted schematically in FIG. 2D. Thus, in one embodiment, the truncated transmembrane region of mgG-2 (t-TMR-mgG-2) has the amino acid sequence of SEQ ID NO: 7.

General Production Methods

In one aspect of the present invention, proteins as herein claimed and described may be produced with recombinant techniques in mammalian host cells, e.g. CHO cells, or other cell lines. Mammalian host cells and cell lines suitable for the recombinant production of various different proteins are well-known in the art and described in the literature.

The cleavage and processing of the gG-2 protein was carried out in a mammalian cell line following transfection with a plasmid containing the gG-2 gene. The results suggest that the cleavage of gG-2 to obtain sgG-2 and the carboxy terminal intermediate/mgG-2 can be carried out by a mammalian protease present in the host cell. The use of such a system provides a ready means of determining the N-terminal and C-terminal ends of the entire sgG-2 and carboxy terminal intermediate/mgG-2 proteins of the present invention. In CHO cells the precursor gG-2 protein is cleaved between Met344 and Ala345, generating the carboxy terminal intermediate/mgG-2 protein (SEQ ID NO: 2 and FIG. 1).

In one aspect of the invention, the protein EXCT4-mgG-2 is produced in mammalian cells, preferably in CHO cells (e.g. by recombinant techniques).

In an aspect of the invention, the protein of the invention (e.g. EXCT4-mgG-2) may be produced synthetically (e.g. as one synthetic peptide or by fusion of synthetic peptides).

In one aspect of the invention, the protein of the invention (e.g. EXCT4-mgG-2) as defined herein can, for example, be unglycosylated (e.g. if produced by synthetic means). Alternatively, the protein of the invention can be glycosylated. For instance, the protein may comprise a mammalian pattern of glycosylation, such as a pattern of glycosylation which may be achieved by expression of the protein in a mammalian host cell, e.g. the protein may correspond to or be similar to the carboxy terminal intermediate as depicted in FIG. 1 (e.g. it may contain high mannose N-glycans and no or limited O-glycosylation), or it may correspond to or be similar to mgG-2 as depicted in FIG. 1 (e.g. it may contain mammalian-type N- and O-glycosylation such as that produced in mammalian cells).

One aspect of the present invention is the protein EXCT4-mgG-2 having an amino acid sequence as defined in SEQ ID NO: 5.

In one embodiment of the present invention, the protein is unglycosylated.

In one embodiment of the present invention, the protein has co-translational and/or post-translational modifications, such as glycosylation, acyl lipidation, phosphorylation, acetylation, methylation, sulfation or hydroxylation. These modifications can be acquired by production in mammalian cells or by site-directed modification in vitro of a synthetic peptide.

One aspect of the present invention is the protein EXCT4-mgG-2 comprising mammalian-type glycosylation.

The exact sequences of gG-2 (and hence carboxy terminal intermediate/mgG-2) vary between naturally occurring isolates of HSV-2. An exemplary amino acid sequence of gG-2 is provided as SEQ ID NO: 1 and corresponds to the sequence of gG-2 in HSV-2 strain 333 as defined by the accession number EU018098.1. An exemplary sequence of an entire carboxy terminal intermediate/mgG-2 is provided as SEQ ID NO: 2 and corresponds to the sequence of the carboxy terminal intermediate/mgG-2 in HSV-2 strain 333. This sequence starts from position 345 of SEQ ID NO: 1, which is the cleavage site when entire gG-2 is produced in CHO cells. However, it will be appreciated that the equivalent position in a different HSV-2 isolate may be located at a slightly different position or have a slightly different sequence, providing that the relevant protease can still act to cleave it. Thus, an exemplary N-terminus of the entire carboxy terminal intermediate/mgG-2 is at position 345 of SEQ ID NO: 1, or its equivalent position in a different HSV-2 isolate. An exemplary C-terminus of the entire carboxy terminal intermediate/mgG-2 is at position 698 of SEQ ID NO: 1, or its equivalent position in a different HSV-2 isolate. Sites of protease action can be predicted by a person skilled in the art. Thus, the N-terminus and C-terminus of the entire carboxy terminal intermediate/mgG-2 for a particular HSV-2 isolate can readily be determined by any suitable method, for example by transfection into a mammalian cell line as described elsewhere herein followed by amino acid sequencing of the produced carboxy terminal intermediate/mgG-2, or by alignment of the gG-2 amino acid sequence of the strain of interest with that of the gG-2 protein of HSV-2 strain 333, such that the corresponding cleavage site may be identified in silico.

Due to the genetic variability of the gG-2 gene among HSV-2 isolates and as the precise cleavage site between sgG-2 and carboxy terminal intermediate/mgG-2 may vary between isolates and in different mammalian cells, exemplary mgG-2 sequences are SEQ ID NO: 2, or an mgG-2 molecule which has a sequence which is at least 90%, for example at least 95%, 96%, 97%, 98% or 99% identical to SEQ ID NO: 2, for example as a result of modifications such as deletion or insertion of amino acids or amino acid substitutions (e.g. conservative amino acid substitutions). Said modified sequences must retain the capability of being used in the invention as defined herein, e.g. must be capable of use in therapy preferably in vaccination or in serodiagnosis of HSV-2 infection, with the features as described elsewhere herein.

Medical Uses

One aspect of the present invention, is a protein as herein described and claimed, such as the protein EXCT4-mgG-2, for use in therapy.

For example, a protein of the invention may be used in the treatment or prevention of a disorder related to HSV-2, namely HSV-2 infection or a disease or disorder related thereto (i.e. a disease or disorder associated with HSV-2 infection). Specifically, the protein may be used as a vaccine, or vaccine antigen, and thus for immunisation or vaccination against HSV-2. Such immunisation or vaccination may have both prophylactic and therapeutic effects, i.e. it may be used to prevent, or reduce the risk of, a HSV-2 infection, or to treat an existing HSV-2 infection.

In one aspect of the invention a protein as herein described and claimed, such as the protein EXCT4-mgG-2, is for use in combination therapy with other active agents, such as agents (therapeutic agents) which are useful in the vaccination or treatment of HSV-2 or HIV.

In one aspect of the present invention, a protein as herein described and claimed, such as the protein EXCT4-mgG-2, may be combined with a second antigen, for example a second HSV-2 glycoprotein such as gB, gC, gD, gE, gH, gI, gK, gL and/or gM or fragments thereof.

In an aspect of the invention, a protein as herein described and claimed, such as the protein EXCT4-mgG-2, may be administered to a patient in combination with at least one other HSV protein such as UL11, UL14, UL16, UL17, UL21, UL36, UL37, UL41, UL46, UL48, UL49, US6, US7, US8, US11, VP13/14, VP16, VP22, VP5, VP19c, VP21, VP23, VP24 and/or VP26.

In an embodiment, a protein as herein described and claimed, such as the protein EXCT4-mgG-2, may be administered to a patient in combination with a second HSV-2 glycoprotein such as gB, gC, gD, gE, gH, gI, gK, gL and/or gM or fragments thereof.

In a further embodiment, a protein as herein described and claimed, such as the protein EXCT4-mgG-2, may be administered to a patient in combination with a HSV protein such as UL11, UL14, UL16, UL17, UL21, UL36, UL37, UL41, UL46, UL48, UL49, US6, US7, US8, US11, VP13/14, VP16, VP22, VP5, VP19c, VP21, VP23, VP24 and/or VP26.

Induction of antibodies is an important humoral defense mechanism during viral infection, for the host to clear the infection. Antibodies recognize specific viral antigenic determinants (epitopes) and can interact with free virions or virus-infected cells. Antiviral effects on free virions include neutralising activity and Fc-mediated complement-mediated lysis and phagocytosis.

Figure 6:
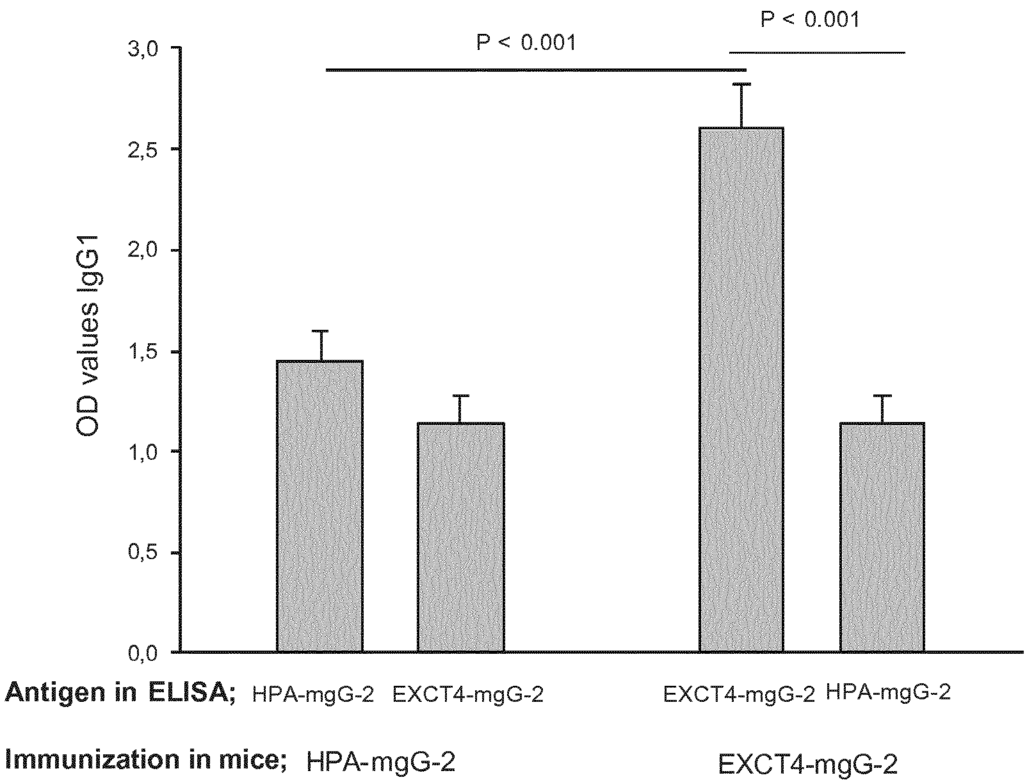
FIG. 6 shows anti-mgG-2 IgG1 antibody responses in serum. Mice were vaccinated with 1 μg of HPA-mgG-2 (n=10) or EXCT4-mgG-2 (n=10)×3 intra-muscularly with CpG and alum as adjuvant. Serum was collected 3 weeks after the third immunization and subjected to an mgG-2-specific ELISA using the same concentration of HPA-mgG-2 or EXCT4-mgG-2 antigen. Optical density values at 1/2430 dilution were analyzed for both groups. Data are from two separate experiments. The error bars indicate mean+SEM.
Figure 7:
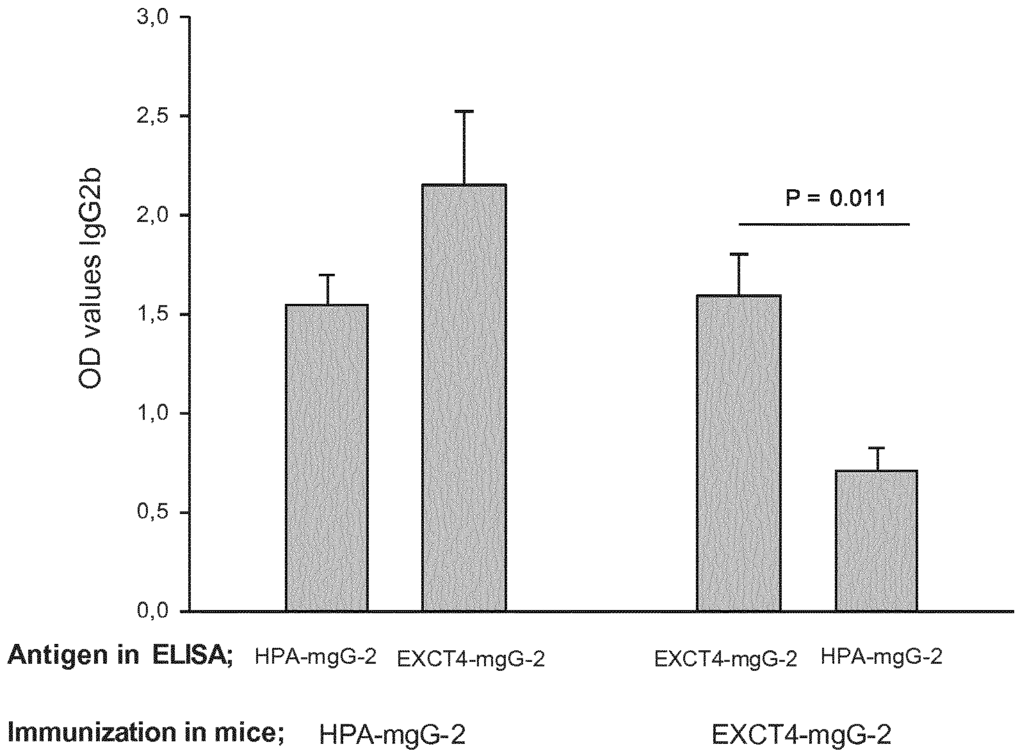
FIG. 7 shows anti-mgG-2 IgG2b antibody responses in serum. Mice were vaccinated with 1 μg of HPA-mgG-2 (n=10) or EXCT4-mgG-2 (n=10)×3 intra-muscularly with CpG and alum as adjuvant. Serum was collected 3 weeks after the third immunization and subjected to an mgG-2-specific ELISA using the same concentration of HPA-mgG-2 or EXCT4-mgG-2 antigen. Optical density values at 1/2430 dilution were analyzed for both groups. Data are from two separate experiments. The error bars indicate mean+SEM.

In the clinical prophylactic vaccine study using gD-2 as antigen, no protection against HSV-2 infection or disease was presented. However, the observed protection against HSV-1 induced disease and infection correlated to antibodies and not to cellular immune responses. A possible explanation to these unexpected findings might be that the neutralization activity was significantly higher against HSV-1 than to HSV-2. The present inventor has recently shown that a robust IgG-antibody response was elicited after vaccination with HPA-mgG-2 in mice, which contributed to protection via antibody-dependent cellular cytotoxicity and complement-mediated cytolysis. As EXCT4-mgG-2 is truncated it was unexpected that the levels of IgG1 antibodies to EXCT4-mgG-2 antigen after EXCT4-mgG-2 vaccination of mice were significantly higher compared with the levels of IgG1 antibodies to HPA-mgG-2 antigen in sera from HPA-mgG-2-vaccinated mice, and that significantly higher IgG1 and IgG2b antibody levels were detected in ELISA when sera from EXCT4-mgG-2-immunized mice were tested for reactivity to EXCT4-mgG-2 antigen as compared with reactivity to HPA-mgG-2 antigen (FIGS. 6-7).

One aspect of the present invention is a protein as herein described and claimed, such as the protein EXCT4-mgG-2, for use in the prevention and/or the treatment of a disorder related to HSV-2.

As used in accordance with the present invention, an HSV-2-related disease or disorder is herein defined as a disease or disorder caused by HSV-2. HSV-2-related disease may include symptoms such as: local genital or extra-genital vesicular or ulcerative lesions; pain; itching; or erythema. An HSV-2 related infection is herein defined as an infection caused by HSV-2, and wherein said virus has established latency in the dorsal root ganglia. HSV-2 can thereafter reactivate and induce clinical symptoms (disease), or be asymptomatically shedded.

In a primary HSV-2 infection, defined as the first time an individual is infected with HSV-2, local symptoms are sometimes accompanied by systemic symptoms such as fever, malaise, myalgia, headache, dysuria, urethritis, pharyngitis, inguinal adenopathy and meningitis.

Several studies using the murine model have shown that CD4+ T-cell proliferation and IFNγ production are key mediators for control of a primary genital infection with HSV-2. Similarly, in murine vaccination models, IFNγ-secreting CD4+ T-cells are crucial for protection (Harandi et al., 2001, Am J Reprod Immunol. vol. 46, 420; Parr and Parr, Immunology, 1999; vol 98, 639; Parr and Parr, Int Rev Immunol., 2003, vol. 22, 43; Iijima et al., J Exp Med. 2008, vol. 205, 3041). Furthermore, vaccinated CD4+ T-cell-deficient mice, which rapidly die after genital challenge, were protected by treatment with exogenous IFNγ. The inventor has shown in two earlier reports that vaccination with HPA-mgG-2 together with adjuvant induces a robust systemic CD4+ T-cell response and IFNγ production. The importance of IFNγ production was further confirmed by using IFNγ gene knockout mice, in that following vaccination with HPA-mgG-2 and CpG as adjuvant such mice were not protected from HSV-2-related disease or death.

Figure 10A:
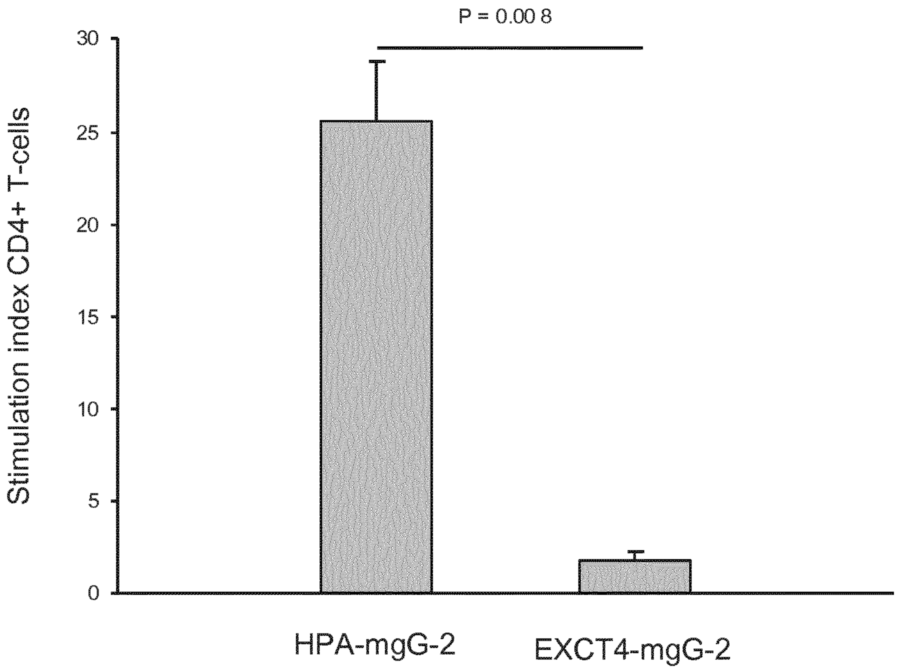
FIG. 10 shows stimulation index (SI) of CD4+ T-cells (A) and IFNγ production of CD4+ T-cells and spleen cells (B). Mice were immunized with HPA-mgG-2 or EXCT4-mgG-2 three times intra-muscularly with CpG and alum as adjuvant. Three weeks after the third immunization spleen cells were collected. Purified CD4+ T-cells and splenocytes were stimulated with HPA-mgG-2 or EXCT4-mgG-2 antigen for 4 days: Proliferation (SI) was measured after addition of thymidine and IFNγ production was quantified by ELISA. Data are mean values from two separate experiments. The error bars indicate mean+SEM.
Figure 10B:
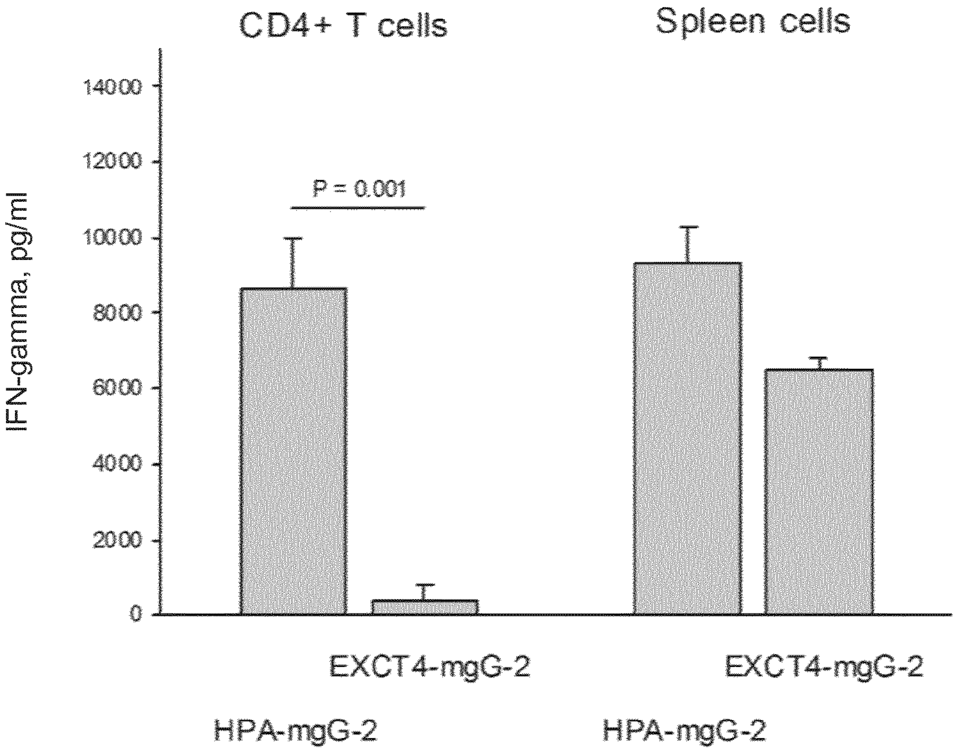

In contrast, immunization of mice with EXCT4-mgG-2 induced no significant systemic CD4+ T-cell proliferation (SI<3, FIG. 10A) and very low IFNγ production (FIG. 10B). However, splenocytes stimulated with EXCT4-mgG-2 antigen produced IFNγ, although in lower amounts, as compared with mice immunized with HPA-mgG-2. It is important to point out that despite these unexpected results the EXCT4-mgG-2 antigen induced 100% survival and minimal genital disease after vaccination when challenged with HSV-2.

Herpes simplex virus establishes latency and a chronic infection in sensory neurons. After a primary infection both non-neutralizing and neutralizing antibodies against several viral proteins as well as CD4+ and CD8+ T-cell responses are elicited. Despite these specific immune responses, HSV-2 is intermittently reactivated, including viral replication, anterograde transport in neurons, infection of the genital epithelial cells and transmission to the next host. It is obvious from an evolutionary standpoint that HSV-2 can cope with these immune responses; otherwise the virus should have been eradicated. The induction of de novo immune responses may therefore be a favorable vaccine strategy as the chance increases that the host can control the virus more effectively. De novo immune responses have been described in the design of therapeutic vaccines for various viruses such as respiratory syncytial viruses, human papilloma viruses and HIV. The protein EXCT4-mgG-2, which induces qualitatively different B- and T-cell responses after vaccination as compared with the HPA-mgG-2 protein, and proteins similar thereto, are therefore promising vaccine candidates.

For a sufficiently effective vaccination in accordance with the invention, it may be advantageous that a protein as herein claimed and described, e.g. EXCT4-mgG-2, has post-translational modifications such as glycosylation. Thus, in one embodiment, the peptide is co-translationally and/or post-translationally glycosylated and the glycosylation is of mammalian-type N- and O-glycosylation. Mammalian cells have the capacity to process high-mannose N-glycans into more complex or branched forms including attachment of for example terminal sialic acid or fucose molecules. In other words, mammalian-type N-glycosylation generally takes the form of mostly complex type N-glycans. Mucin-type O-glycosylation is initiated by attachment of a GalNAc residue to the hydroxyl group of serine or threonine (forming the Tn-antigen). In other words, in mucin-type O-glycosylation GalNAc is the first sugar which is added. Elongation of the sugar chain in mammalian cells is usually obtained by addition of for example galactose (T-antigen) or N-acetylglucosamine followed by addition of for example sialic acid to form complex sugar chains. The high number and clusters of Tn-antigens in HPA-mgG-2 is a prerequisite of binding specifically to *Helix pomatia* lectin with low affinity to other lectins. A cluster is herein defined as single GalNAc residues on closely located multiple serine or threonine amino acids.

The protein EXCT4-mgG-2 produced in CHO cells is different regarding the glycan content as compared with HPA-mgG-2, as EXCT4-mgG-2 has no affinity to Helix pomatia lectin. In the extracellular region of mgG-2, there are 69 serine or threonine residues which are potential sites for O-glycosylation and which are mostly clustered to the N-terminal portion of mgG-2. The following amino acid positions in mgG-2 are O-glycosylated after infection of Vero cells with HSV-2 (strain 333); 353-356, 362, 449, 453-454, 460, 463, 499, 585, 602, and 615. CHO cells are known to express core 1 glycans, which include GalNAc residues followed by addition of galactose. This structure is often terminated by addition of sialic acid. However, the precise number and location of Tn-molecules or other glycans in EXCT4-mgG-2 produced in CHO cells is not known.

Alternatively, the mammalian-type glycosylation referred to herein can be carried out in vitro by site-directed addition of appropriate N- and/or O-glycans. Thus, one production method relates to in vitro site-directed O-glycosylation of the present protein, e.g. EXCT4-mgG-2, leading to identical or similar glycan residues as produced in mammalian cells. In one aspect of the invention, the protein, e.g. EXCT4-mgG-2, may be produced by in vitro site-directed O-glycosylation, which is designed to result in identical or similar glycan residues to those produced in mammalian cells. Such design can readily be carried out by a person skilled in the art with knowledge of the structure and composition of the glycans found in mammalian glycosylation. For example, in this way it is possible to mimic O-glycosylation production in mammalian cells by adding clusters of single GalNAc residues and/or complex O-glycans as described elsewhere herein. Such in vitro site-directed O-glycosylation can be carried out using methods described in the art. The goal is to incorporate single-GalNAc residues into non-O-glycosylated proteins (e.g. EXCT4-mgG-2) so they correspond to native counterparts produced in mammalian cells. The initiating step of O-glycosylation is the addition of the monosaccharide GalNAc to the hydroxyl group of serine and threonine residues. This reaction is catalyzed by at least 20 different isoforms of GalNAc transferases which display different patterns of tissue-specific expression. The primary amino acid sequence is also of importance for determining substrate specificity of the GalNAc transferase enzymes. These enzymes are produced as soluble, secreted, purified recombinant human GalNAc transferases expressed in insect cells. The selection of the appropriate GalNAc transferase isoform is based on a screening assay of substrate specificities using 15-20 mer synthetic peptides covering O-glycan acceptor sites to the mgG-2 proteins. Non-O-glycosylated mgG-2 protein may be expressed in bacteria, yeast or baculovirus. The proteins of the gG-2 proteins may also be produced chemically. These target molecules are mixed with UDP-GalNAc and GalNAc transferase as described.

One aspect of the present invention is a method for producing an HSV-2 vaccine, whereby a host cell is transfected with an expression vector, e.g. a plasmid, comprising a nucleotide sequence which encodes a truncated mgG-2 protein of the invention, as defined herein, (e.g. a truncated gene from an HSV-2 strain encoding a protein as herein described and claimed). In an embodiment of the invention, the host cell may be selected from the group consisting of CHO, HEK293, CAP and PER.C6 cells.

In one alternative embodiment, in vitro site-directed O-glycosylation is used for attaching glycans to mgG-2 proteins as defined and claimed herein.

A further aspect of the present invention provides the use of a protein as herein described and claimed, such as the protein EXCT4-mgG-2, for the manufacture of a medicament for use in the treatment or prevention of a HSV-2 related disorder, or in vaccination.

The present invention also provides the use of a protein as herein described and claimed, such as the protein EXCT4-mgG-2, for use in therapy. By therapy as herein defined is meant any treatment of a subject to prevent or treat a disease. Treatment of a disease may be curative, prophylactic or palliative, or may improve the condition of the subject or relieve the subject's symptoms. In particular, the proteins of the present invention may be used in the treatment of an HSV infection, particularly an HSV-2 infection or an HSV-2 related disease.

A further aspect of the present invention is a method of vaccination, whereby a protein as herein described and claimed, such as the protein EXCT4-mgG-2, is administered to a subject in need of such vaccination. Such a method of vaccination may be used to prevent or treat HSV infection in the subject, particularly to prevent or treat HSV-2 infection or an HSV-2-related disease.

In one aspect of the present invention, a therapeutically effective amount of a protein as herein described and claimed is administered to a subject in need of vaccination, for instance a subject in need of vaccination against HSV-2. The "therapeutically effective amount" for use in accordance with the invention, is an amount of a protein as herein described and claimed, such as the protein EXCT4-mgG-2, optionally together with any other desired active ingredients, to enable the therapeutic or vaccination effects as described elsewhere herein. In such methods of vaccination or therapy, efficacy of treatment can take the form of reduction in symptoms of disease (e.g. genital lesions), or reduction of genital shedding of virus, or reduction in progression of disease, as well as cure of disease. As vaccination is involved, prophylactic effects or treatments, e.g. prevention or protection against infection, or symptoms of disease, are also included.

One aspect of the present invention is the use of a protein of the invention, such as EXCT4-mgG-2, in vaccination, including vaccination against HSV-2.

An aspect of the invention provides a vaccine comprising a protein as herein described and claimed, particularly the protein EXCT4-mgG-2, optionally together with one or more adjuvants.

An aspect of the present invention is a vaccine or a pharmaceutical composition comprising a protein as herein described and claimed, such as the HSV-2-derived protein EXCT4-mgG-2, optionally together with one or more adjuvants, pharmaceutically-acceptable carriers or excipients, such as a stabilizer, buffer, surfactant, salt and/or preservative. Said compositions may optionally further comprise other active (therapeutic) agents as described elsewhere herein.

According to one embodiment, a composition comprising a protein of the invention and one or more components selected from a group consisting of an adjuvant, stabilizer, buffer, surfactant, salt and/or preservative is provided.

The invention herein disclosed further relates to the use of a protein of the present invention, e.g. EXCT4-mgG-2, as an antigen to induce immunity to HSV-2, for usage as a prophylactic and/or therapeutic vaccine. A prophylactic vaccine is defined as a vaccine which can give protection against HSV-2 infection and/or disease and/or reduce viral shedding of HSV-2. A therapeutic vaccine is defined as a vaccine which can reduce the symptoms from HSV-2-induced disease and/or reduce viral shedding of HSV-2. Thus, treatment of HSV-2 infection enabled by the vaccine compositions of the present invention can involve prevention of HSV-2 infection, or reduction of symptoms of disease, or prevention or reduction of viral shedding of HSV-2.

Thus, in a further aspect of the invention, a protein as herein described and claimed, such as EXCT4-mgG-2, can be used as a prophylactic or therapeutic vaccine.

An aspect of the invention is the use of a protein as herein described and claimed, such as EXCT4-mgG-2, for the treatment and/or prevention of an HSV-2-related disease and/or infection, as herein described and claimed. As HSV-2 infection is linked to an increased risk of HIV infection, the use of the present invention in the treatment or prevention of HSV-2 infection or disease should also be useful to prevent or reduce HIV infection.

The vaccine or vaccine composition can include the above-mentioned protein EXCT4-mgG-2, and might include one or more further components such as adjuvant, stabilizer, buffer, surfactant, salt and/or preservative.

The invention described herein includes a subunit vaccine. This type of vaccine has a better safety profile compared to traditional attenuated live virus vaccines; however, subunit vaccines present the drawback of only having a limited immunogenicity. Therefore, subunit vaccines generally need an adjuvant to enhance the immune response. As part of the invention herein, the vaccine might include an adjuvant together with the antigen molecules of the present invention. A preferred adjuvant will enhance a Thl cell response. In one embodiment the adjuvant comprises CpG-containing nucleotides. In one embodiment the adjuvant comprises nanocrystalline particles of inulin. In one embodiment the adjuvant comprises saponins together with immunostimulating complexes (ISCOMs). In one embodiment the adjuvant includes different aluminium salts such as alum. In one embodiment the adjuvant comprises monophosphoryl lipid A (MPL), or a combination of MPL with aluminium salt. In one embodiment the adjuvant comprises MF59. In one embodiment the adjuvant comprises flagellin. In one embodiment the adjuvant comprises an immune-stimulating cytokine. In one embodiment the adjuvant comprises squalene. In one embodiment the adjuvant comprises a TLR ligand, such as a TLR9 ligand. In one embodiment the adjuvant comprises a TLR9 ligand combined with an antimicrobial peptide such as KLKLLLLLKLK (SEQ ID NO: 14). In one embodiment the adjuvant comprises liposomes or virosomes. In one embodiment the adjuvant is composed of a nanoemulsion. In one embodiment the adjuvant is composed of polylactic-co-glycolic acid (PLGA). In one embodiment the adjuvant activates antigen-presenting cells (APCs). In one embodiment of the invention, two or more of the above-mentioned adjuvants are combined. The adjuvant can be used as a component in the vaccine mixed with the antigen. The adjuvant can also be fused or covalently bound to the antigen.

The subject to which the vaccine can be given may be a human subject. The vaccine can be given to men and women, children and adults as a therapeutic and/or prophylactic vaccine. The route of administration can be intramuscular, intradermal, subcutaneous, mucosal, intravenous, intraperitoneal, transdermal, subdermal, intracranial, intranasal, anal, vaginal, oral, sublingual or inhaled, according to methods described in the art. The vaccine can be given as a single dose or multiple doses, e.g. two, three, four, five times or more. A booster dose may be given within 1 month, from 1-12 months or more than 1 year after the initial vaccination. Each dose of the vaccine will contain the amount of antigen needed to induce a good therapeutic and/or prophylactic effect. In an embodiment of the invention, the number of doses is 1-3. The vaccine can be provided as a solution, a solid or as a powder (e.g. a lyophilized form).

In one embodiment, a protein in accordance with the present invention is formulated for administration as a single dose or multiple doses, such as two, three, four or five doses.

The optimal amount of antigen in the vaccine composition can readily be determined by a person skilled in the art. An effective dose of the antigen may be from 0.5-1000 μg. In an embodiment of the invention, an effective dose of the antigen may be from 20-200 μg. In an embodiment of the invention, an effective dose of the antigen may be from 50-100 μg of antigen. The dose of antigen will depend on the composition of the antigen and choice of adjuvant. It can also depend on the age, weight and condition of the vaccinated subject. The dose of antigen and adjuvant in a therapeutic vaccine can differ from the dose used in a prophylactic product.

In one embodiment, an effective dose of a protein as herein claimed and described, may be from 0.5-1000 μg, such as from 20-200 μg, or from 50-100 μg.

The protein can also be provided in the form of nucleic acids encoding the protein as defined herein. Any appropriate form of nucleic acid may be used, e.g. a DNA vector such as a plasmid. Alternatively, a viral vector containing the nucleic acid molecule may be used, or the nucleic acid molecule may be administered in the form of lipoplex or polyplex particles, according to principles and techniques well known in the art.

Figure 5:
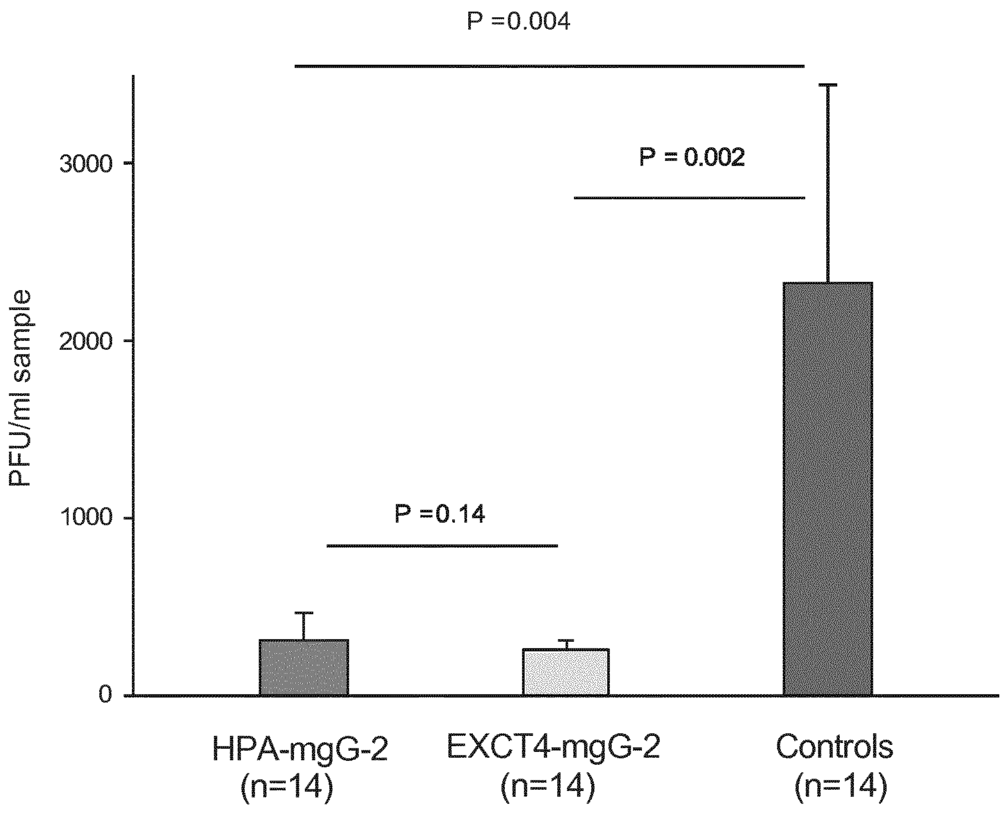
FIG. 5 shows the plaque-forming units (PFU) in vaginal washes at day 2 after challenge with 100,000 PFU of HSV-2 strain 333. Mice were vaccinated with 1 μg of HPA-mgG-2 or EXCT4-mgG-2×3 intra-muscularly with CpG and alum as adjuvant and compared with unvaccinated controls. Data are from two separate experiments. The error bars indicate mean+standard error of the mean (SEM).

In one embodiment of the invention, the effect of a protein as herein claimed and described, e.g. EXCT4-mgG-2, involves a decrease in local HSV-2 replication, for example in the vagina. In mice vaccinated with the protective HPA-mgG-2 or EXCT4-mgG-2, HSV-2 replicated in the vagina with significantly lower titers as compared with the controls (FIG. 5). After challenge of non-vaccinated control mice, HSV-2 ascends from the genital site to the sensory dorsal root ganglia, spinal cord and central nervous system inducing deadly encephalitis. Thus, the inventor has evidence that EXCT4-mgG-2 can induce protection useful in vaccination.

In an embodiment of the invention, the effect of a protein as herein described and claimed, e.g. EXCT4-mgG-2, involves production of specific antibodies, for example the subclasses IgG1, IgG2b and IgG2c.

The terms "decrease" or "reduce" or "increase" (or equivalent terms) as used herein include any measurable decrease or reduction or increase (as appropriate) when compared with an appropriate control. Appropriate controls would readily be identified by a person skilled in the art and might include non-treated or non-vaccinated individuals or individuals subjected to a treatment which was different to that defined in the present invention (or a population thereof), or might include a level of a particular parameter in the same individual subject measured at an earlier time point (e.g. comparison with a "baseline" level in that subject). Preferably the decrease or reduction or increase will be significant, for example clinically or statistically significant. Methods of determining the statistical significance of differences in levels of a particular parameter are well known and documented in the art. For example, herein a decrease or increase in level of a particular parameter is generally regarded as significant if a statistical comparison using a significance test such as a Student t-test, Mann-Whitney U Rank-Sum test, chi-square test or Fisher's exact test, as appropriate, shows a probability value of $<0.05$.

The terms "patient" and/or "subject" as used herein are interchangeable and include any mammal, for example humans and any livestock, domestic or laboratory animal. Specific examples include mice, rats, guinea pigs, pigs, cats, dogs, sheep, rabbits, cows and monkeys. Preferably, however, the patient is a human subject.

Sequence identity (% SI) as used herein may be assessed by any convenient method. However, for determining the degree of sequence identity between sequences, computer programs that make multiple alignments of sequences are useful, for instance Clustal W (Thompson et al., Nucleic Acids Res. 1994 vol. 22, 4673). Other methods to calculate the percentage identity between two amino acid sequences are generally art-recognized and include, for example, those described by Carillo and Lipton (SIAM J. Applied Math., 1988, vol. 48, 1073).

Generally, computer programs will be employed for such calculations. Programs that compare and align pairs of sequences, like ALIGN (Myers and Miller, CABIOS, 1988, vol. 4, 11), FASTA (Pearson, Methods in Enzymology, 1990, vol. 183, 63) and gapped BLAST (Altschul et al., Nucleic Acids Res., 1997, vol. 25, 3389), or BLASTP (Devereux et al., Nucleic Acids Res., 1984, vol. 12, 387) are also useful for this purpose. If no such resources are at hand, according to one embodiment sequence identity (% SI) can be calculated as (% SI)=100%*(Nr of identical residues in pairwise alignment)/(Length of the shortest sequence), as a rule of thumb.

By way of providing a reference point, sequences according to the present invention having at least 90%, 95%, 96%, 97%, 98% or 99% identity may be determined using the ALIGN program with default parameters (for instance available on Internet at the GENESTREAM network server, IGH, Montpellier, France).

Proteins of the invention with less than 100% amino acid identity relative to the herein-defined reference sequences may be modified relative to the reference sequence by substitution, addition or deletion of an appropriate number of amino acids. When a protein of the invention contains an amino acid substitution relative the relevant reference sequence, the substitution is preferably a conservative amino acid substitution. The proteins of the present invention may also include modified amino acids. Amino acid modifications may include, for instance, phosphorylation, acetylation, methylation, amidation or any other amino acid modification known in the art, so long as the protein retains the desired characteristics.

The term "conservative amino acid substitution", as used herein, is one in which an amino acid residue is replaced with another amino acid residue having a similar side chain. Families of amino acid residues having similar side chains have been defined in the art, including basic side chains (e.g. lysine, arginine, histidine), acidic side chains (e.g. aspartic acid, glutamic acid), uncharged polar side chains (e.g. asparagine, glutamine, serine, threonine, tyrosine), non-polar side chains (e.g. glycine, cysteine, alanine, valine, leucine, isoleucine, proline, phenylalanine, methionine, tryptophan), beta-branched side chains (e.g. threonine, valine, isoleucine) and aromatic side chains (e.g. tyrosine, phenylalanine, tryptophan, histidine).

With respect to the above description, it is to be realized that the features of the invention, including variations in size, materials, shape, form, function and manner of operation, production and use, are deemed readily apparent and obvious to one skilled in the art. Therefore, the foregoing is considered as illustrative only of the principles of the invention. Further, since numerous modifications and changes will readily occur to those skilled in the art, all suitable modifications and equivalents may be resorted to, falling within the scope of the invention.

All prior art documents cited in this application are incorporated by reference in their entirety.

EXAMPLES

The present invention is further illustrated by the following non-limiting examples. The examples should not be interpreted as limiting the scope of the invention.

The state of the art for production of subunit vaccines is to use truncated proteins, i.e. proteins where the transmembrane region (TMR) has been removed to facilitate the production process and secretion of the protein into the cell medium.

The inventor has produced full-length mgG-2 from virus-infected cells using affinity chromatography with *Helix pomatia* agglutinin lectin and by immunosorbent purification using anti-mgG-2 monoclonal antibodies. Purification of HPA-mgG-2 from virus-infected cells is tedious, and generates only low amounts of protein.

For example, to produce 25 ml packed HSV-2 infected BHK-cells, followed by solubilization with detergent and purification with HPA, takes approximately 2 months generating approximately 2 mg of mgG-2. When using the same amount of virus lysate for immunosorbent purification, 100 μg of mgG-2 is obtained. Thus, neither of the methods are suitable for scale-up production.

In contrast, using recombinant techniques in CHO cells to produce the protein EXCT4-mgG-2 is much more effective and several milligrams of purified protein can be produced in a few weeks. The production is therefore suitable for production of larger amounts of protein.

Example 1

Production and Purification of mgG-2 Proteins from CHO Cells with Recombinant Technique Methods A. Extracellular Region of mgG-2 (EX-mgG-2, FIG. 2B)

The complete nucleotide sequence of the extracellular domain of mgG-2 of HSV-2 strain 333 (SEQ ID NO: 15) was cloned into the pcDNA6/myc-His vector. In initial expression experiments in CHO cells we observed that the extracellular-region of mgG-2 was extremely hydrophilic, so that it was difficult to detect the protein in the medium by Coomassie blue staining, Alcian blue staining or Western blot. The gG-2 sequence was therefore cloned into the pSMIIgG2 plasmid using NheI and BamHI sites including an enterokinase site between the gG-2 sequence and the IgG2 sequence. Medium from transient transfection of CHO-K1 cells was purified using the carboxy terminal-located His-tag.

B. Extracellular Region of mgG-2 Fused with the Intracellular Region without Amino Acids Encompassing TMR (EXCT0-mgG-2, FIG. 2C)

The EXCT0 sequence derived from the HSV-2 strain 333 (SEQ ID NO: 16) was first cloned into pUC57 using the EcoRI/HindIII restriction sites and transferred into the mammalian expression pTT5 vector. Transient transfection was performed using lipofectamine 2000 as transfection reagent and the protein was expressed in suspensions of CHO cells and HEK293 cells (GenScript). We observed in the purification process that the binding of the carboxy terminal His-tag to the Ni purification medium was weak. Instead, anion ion exchange and gel filtration columns were used. The detailed purification process is described below.

C. Extracellular Region of mgG-2 Fused with Four Amino Acids of TMR and the Intracellular Region (EXCT4-mgG-2, FIG. 2D)

Construction of an Expression Plasmid

The DNA sequence for EXCT4-mgG-2 (SEQ ID NO: 17) was derived from HSV-2 strain 333. The designed construct was synthesized by Eurofins MWG (Ebersberg) and cloned into the pcDNA6/myc-His vector (Life Technologies) using Hind III and AgeI, which also removed the myc-epitope. The authenticity, frame and orientation of the construct were verified by DNA sequencing (Eurofins MWG Operon, Ebersberg). Transfection and cloning of EXCT4-mgG-2-producing CHO cells CKO-K1 cells (ATCC) were grown in Iscove's Modified Dulbeccos's Medium supplemented with 10% fetal bovine serum (IMDM+FBS) (Lonza). Cells were cultured in a humidified incubator at 37° C. with 5% $CO_2$ atmosphere and transfected with 4 μg of pcDNA6/EXCT4-mgG-2/His DNA and lipofectamine 2000 (Invitrogen). Transfected cells were selected with the addition of 10 μg/ml of Blasticidin-HCl (Invitrogen). Supernatants and lysates were analyzed by Western blot for the presence of recombinant EXCT4-mgG-2 and the clone secreting the highest amount of EXCT4-mgG-2 was selected for another round of cloning. The clone of choice was expanded to three T175 flasks. The cells were trypsinized, washed with PBS and resuspended in 100 ml of ProCHO4 with 1× ProHT, 4 mM 1-glutamine and 2% FBS (Lonza) in a 250 ml spinner flask (Bellco). Cells were passaged every 3-5 days and FBS was gradually removed until the cells were adapted to serum-free suspension growth.

Production of EXCT4-mgG-2 in a Bioreactor Perfusion Culture

Cells were cultured in 1.5 L in a 3 L Biobundle bioreactor (Applikon Biotechnology, Netherlands) at 37° C. with a stir rate of 100 rpm at a pH of 6.9 and pO2 set-point of 40% of air saturation. The perfusion rate was between 0.3 and 0.8 dilutions per day and medium was harvested and centrifuged at 8000×g for 30 min at 4° C., pre-filtered through a 0.45 μm Mini Capsule Filter (Pall Corporation), and concentrated using tangential flow filtration with a Pellicon-2 system (Millipore) equipped with one Pellicon 2 PLCGC regenerated cellulose filter with a molecular weight cut-off of 10 kDa. The buffer was exchanged to PBS.

An Alternative Production Method which Increased the Yield of Produced EXCT4

The EXCT4-mgG-2 coding sequence (SEQ ID NO: 17) was amplified by PCR as described above and subcloned into pEE12.4 (Lonza) using Hindlll and RsrII. CHO-K1 (028-W4) cells provided with the GS expression system (Lonza) were grown in DMEM GlutaMax, including 10% foetal bovine serum (FBS) (Gibco, Life Technologies) and seeded in three wells of a six-well plate ($0.5\times10^6$ cells/well). After 24 h, the medium in the three wells was exchanged to L-glutamine-free DMEM (Gibco Thermo Scientific) supplemented with 1×GSEM-supplement (Sigma, Ayrshire UK), 1 mM pyruvate and 10% dialyzed foetal bovine serum (Gibco, Life Technologies). A transfection mix was prepared containing 1 ml supplemented glutamine-free DMEM as described above but without foetal bovine serum, 20 μl of lipofectamine 2000 and 8 μg of pEE EXCT/4 His plasmid. The mix was incubated in room temperature for 20 min and finally 0.5 ml of the mix was added to two of the three wells with CHO-K1 cells. The third well was used as a negative control. After 24 h the selection agent L-methionine sulfoximine (MSX), (Sigma-Aldrich) was added at a concentration of 50 μM. After 48 h the supernatant was harvested from one of the transfected wells. The transfected cells in the parallel positive well were trypsinized and seeded in a tenfold dilution series to obtain single cell colonies. After 10 days 30 colonies were selected and transferred to individual wells and further grown in L-glutamine free, supplemented DMEM including 50 gM MSX. At confluency, the supernatants were analysed for presence of EXCT4/His by Western blot.

Selection of an EXCT4-mgG-2 Expressing Clone and Adaptation to Serum-Free Suspension Growth The highest producing clone was seeded into a 6-well plate containing L-glutamine-free supplemented DMEM including 50 μM MSX. Cells were kept under MSX selection pressure for ~30 days while monitoring confluency and expression was detected by Western blot. Two fully confluent 175 $cm^2$ T-flasks were trypsinized and transferred to a 250 ml spinner flask (Bellco, Vineland, N.J.) containing 75 ml of L-glutamine-free, supplemented DMEM, 25 ml CD FortiCHO (Gibco, Thermo Fisher Scientific, USA) and 50 μM MSX. The flask was incubated in a humidified incubator at 37° C. with 5% $CO_2$ with a stirring rate of 90 rpm with a slightly open lid. The culture was sub-cultured and medium was exchanged 1-2 times/week aiming at keeping the cell density higher than $0.3\times10^6$ cells/ml and the viability higher than 90%. The proportion of FortiCHO was increased stepwise to 100% during a period of four months. At the end of adaptation, a cell concentration of $2\times10^6$ cells/ml could be reached. Spent FortiCHO medium was collected and kept at −20° C.

Purification of EXCT4-mgG-2

200 ml of concentrated medium was run over an ion exchange column Hiprep16/10QFF (Pharmacia) using a peristaltic pump at +4° C. The column was washed with 40 ml Tris-HCl pH 8.2 and then connected to an ÄKTA purifier (Amersham Pharmacia Biotech, UK). The EXCT4-mgG-2 protein was eluted using a gradient from 0 to 100% Tris-HCl pH 8.2 with 1 M NaCl. Selected fractions were pooled and the protein was concentrated in a Vivaspin 20 (GE Healthcare, UK) with a MWCO of 10 kDa at 3900×g for a total of 60 min at +4° C. The concentrated protein was filtered through a Costar Spin-X column with a pore size of 0.45 μm (Corning) and run over a Superose 12 HR 10/30 gel filtration column (Pharmacia) at a flow rate of 0.3 ml/min. Fractions were analysed with UV-cord chromatogram at $OD_{280}$ nm and analysed by Western blot and SDS-PAGE gels stained with Imperial Stain (Thermo Scientific) and with Alcian blue 8GX (Sigma Aldrich). The protein was concentrated with a Vivaspin 20, (GE Healthcare) and diluted in PBS. The protein concentration was measured by BioRad Protein Assay.

Detection of Proteins with Western Blot Analysis

Protein samples were mixed with SDS-PAGE sample buffer containing 100 mM dithiothreitol and heated to 95° C. for 5 min prior to separation on a NuPAGE Bis-Tris 4-12% gel using MOPS-buffer (Invitrogen). The separated proteins were transferred onto a 0.22 μM nitrocellulose membrane (Bio-Rad) or an Immobilon PVDF membrane (Merck Millipore) using a submarine blot cell Novex, XCell II (Invitrogen) with blotting buffer containing 25 mM Tris, 192 mM glycine and 10% methanol. The membrane was blocked in 2% bovine serum albumin (Sigma Aldrich) and then incubated with the in-house anti-mgG-2 monoclonal mouse antibody O1.C5.B2 as primary antibody and an alkaline-phosphatase-labelled goat anti-mouse-IgG antibody (Southern Biotech) diluted 1:1000. The bands were visualized with BCIP/NBT (Southern Biotech).

Cell Toxicity Test

The antigens were tested for cytotoxicity on GMK-AH1 cells using the cell proliferation kit CellTiter 96® $AQ_{ueous}$ One Solution Cell Proliferation Assay (Promega, US) according to the manufacturer's protocol. Potential endotoxin activity was analysed by Endochrome-K reagent (Charles River, Charleston, S.C.).

Results

The EX-mgG-2-IgG2 protein was readily detected in by Coomassie blue staining, Alcian blue staining and WB with an estimated molecular mass of 125 kDa. The protein was extracted from an Immobilon PVDF membrane (Merck Millipore) for N-terminal Edman degradation sequencing. According to the sequence analysis the first amino terminal part of mgG-2 included the amino acids ALTED. For vaccination purposes the IgG2 molecule was cleaved off by Enterokinase Max (Invitrogen) and removed by a Protein A column. Two EXCT0-mgG-2 proteins were readily detected in Coomassie blue staining and WB with estimated molecular masses of 85 kDa and 60 kDa, respectively. Estimated from the WB reactivity most of produced EXCT0-mgG-2 was highly glycosylated (85 kDa). The EXCT4-mgG-2 was detected as a single band in Coomassie and Alcian blue staining and WB with an estimated molecular mass of 90 kDa. All recombinantly produced mgG-2 proteins contained<5 IU/mg protein of LPS and no toxic effect was measured in the cell toxicity assay.

Example 2

HPA-mgG-2 and EXCT4-mgG-2 Antigens Confer Complete Protection After Vaccination in an Animal Model Methods Immunization Antigens The native entire mgG-2 protein was produced by HPA lectin affinity chromatography as described (Olofsson, S. et al., J Virol. 1981, vol. 38, 564; Liljeqvist, J. A. et al., J Gen Virol. 1998, vol. 79, 1215). The antigen was characterized recently and showed high purity, lack of other cross-reactivity with other HSV-2 proteins, as determined by WB and by ELISA using HSV-1 positive sera, no cell toxicity, and no endotoxin contamination (Gorander, S. et al., J Virol. 2012, vol. 86, 7544). The EX-mgG-2, the EXCT0-mgG-2 and EXCT4-mgG-2 antigens were produced as described in Example 1.

Mice

Female 6-8 week old C57BL/6 mice were used in all experiments. The mice were purchased from Harlan Lab., Holland. Mice were anesthetized with 3% isoflurane (Baxter). This study was carried out in accordance to the rules stated by the Swedish board of agriculture. All animal experiments were approved by the ethical board in Gothenburg (Dnr 171-2013).

Adjuvant

Synthetic oligodeoxynucleotides with complete phosphorothioate backbone containing two optimal mouse CpG motifs (ODN1826, TCC ATG ACG TTC CTG ACG TT, SEQ ID NO: 18), (Operon Biotechnologies, USA) and aluminium hydroxide (Alhydrogel, Brenntag, Denmark) were used as adjuvant.

Immunization and Challenge

C57BL/6 mice were immunized by administering three intra-muscular (im) injections into the caudal thigh muscle at 10-day intervals. Each dose contained 1 μg mgG-2, 20 μg CpG and 250 μg alum diluted in phosphate buffered saline (PBS). One control group was immunized im with PBS alone, one control group with CpG and alum alone and one control group with antigen alone without adjuvant.

Six days before challenge the mice were injected subcutaneously with 3 mg of medroxyprogesterone (Depo-Provera, Pfizer, US). Mice were challenged intra-vaginally with $1\times10^5$ PFU (25×50% lethal dose of strain 333) of HSV-2. Vaginal inflammation and disease were graded as follows: healthy (score, 0), genital erythema (score, 1), moderate genital inflammation with blisters (score, 2), severe and purulent genital lesions with loss of hair (score, 3), and hind-limb paralysis and/or general bad condition (score, 4).

Quantification of HSV-2 in Vaginal Washes

Vaginal washes were collected two days post challenge and infectious HSV-2 (PFU) were quantified by a plaque assay on GMK-AH1 cells.

Statistics

SigmaPlot 12.5 software for Microsoft Windows was used for statistical calculations. One-way ANOVA on ranks was used for HSV-2 titres and Fisher's exact test was used for survival data.

Results

Figure 4:
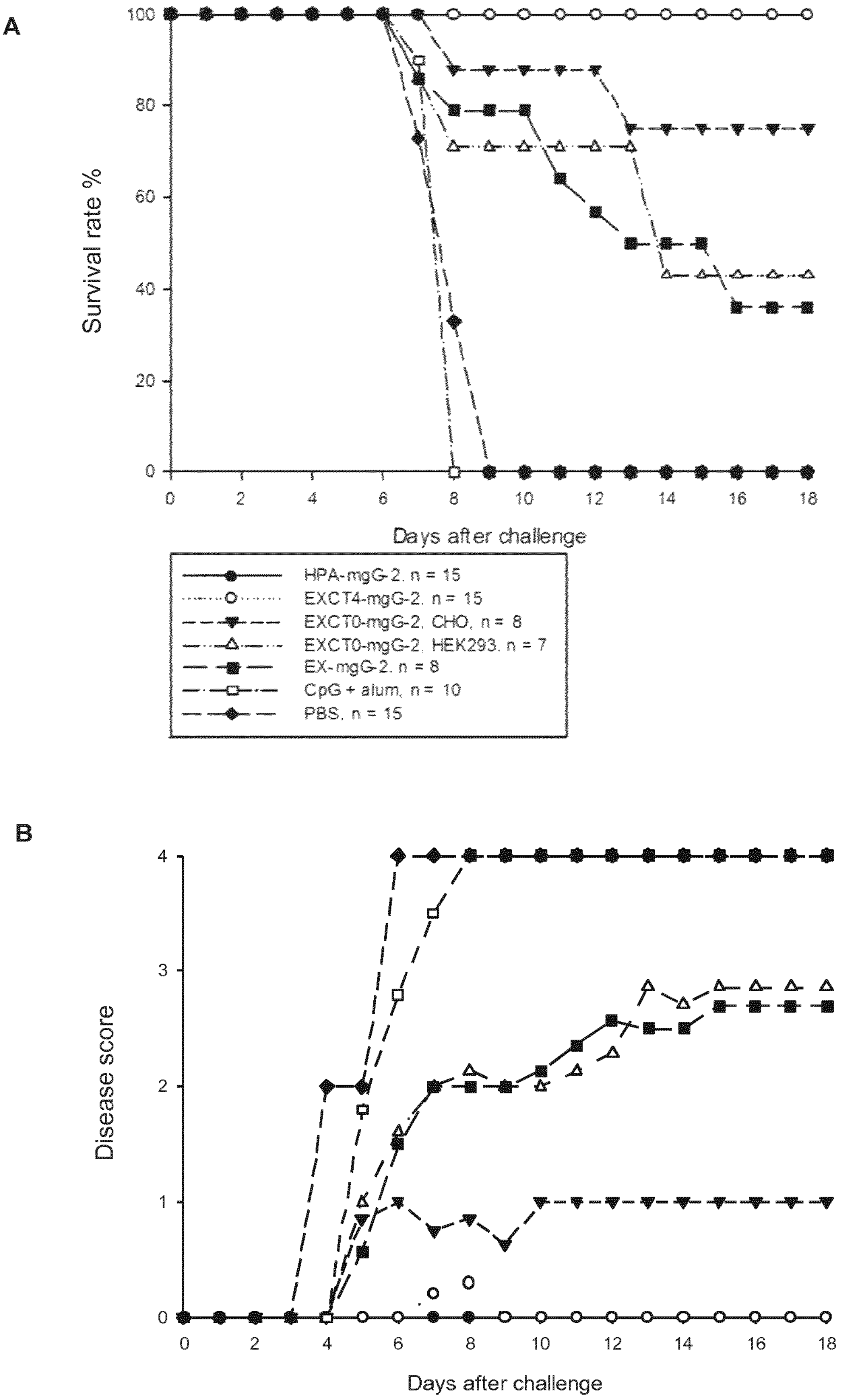
FIG. 4 shows the survival rate (A) and disease score (B) of immunized C57BL/6 mice after challenge with 100,000 plaque-forming units (PFU) of the HSV-2 strain 333 (25× 50% lethal dose at day 0). Mice were immunized three times intra-muscularly with 1 μg of antigen and CpG and alum as adjuvant. i) Native entire mgG-2 produced from virus-infected mammalian cells and purified with *Helix pomatia* agglutinin lectin (HPA-mgG-2), ii) extracellular region of mgG-2 produced recombinantly in CHO cells (EX-mgG-2), iii) extracellular region fused with the intracellular region of mgG-2 produced recombinantly in CHO cells (EXCT0-mgG-2, CHO) and in HEK293 cells (EXCT0-mgG-2, HEK293), iv) extracellular region fused with the intracellular region and four amino acids of transmembrane region of mgG-2 produced recombinantly in CHO cells (EXCT4-mgG-2), v) controls including only CpG and alum, only PBS and only antigens without adjuvant (the outcome for these groups are represented by the PBS group). Data are from two separate experiments.

As shown in FIG. 4, native HPA-mgG-2, produced from virus-infected mammalian cells, and recombinantly produced EXCT4-mgG-2 together with CpG and alum, induced complete protection from death (FIG. 4A) and minimal genital disease scores (FIG. 4B) after vaginal challenge with a fully virulent HSV-2 strain. In contrast, vaccination with EX-mgG-2 in CHO cells gave a significantly lower survival rate, (P=0.0006, FIG. 4A) and higher disease scores (FIG. 4B). Vaccination with EXCT0-mgG-2 produced in CHO cells induced a 75% survival rate, and EXCT0-mgG-2 produced in HEK293 cells induced a 43% survival rate and higher disease scores as compared with vaccination with HPA-mgG-2 or with EXCT4-mgG-2. When data for mice vaccinated with EXCT0-mgG-2, produced in CHO cells (n=8), and in HEK293 cells (n=7), were merged and analysed together, there was a significantly lower survival rate (P=0.017) as compared with EXCT4-mgG-2 immunized mice (n=15). All mice in the control groups died between day 8 and day 9, (antigens without adjuvant are represented by the PBS control graph (FIG. 4A-B), implying that the mgG-2 antigens are not effective without adjuvant and that the adjuvant CpG and alum induced no protection per se. As EXCT4-mgG-2 induced similar protection rate and reduction of disease score as compared with HPA-mgG-2 antigen, the inventor compared immune parameters after vaccination between these two antigens.

Viral Load in Vaginal Washes

HPA-mgG-2- and EXCT4-mgG-2-vaccinated C57BL/6 mice showed similar and statistically significant reductions of viral titres (mean 320 PFU in the HPA-mgG-2 group and 250 PFU in the EXCT4-mgG-2 group) as compared with unvaccinated controls (mean 2320 PFU, FIG. 5).

Example 3

Recombinantly Produced EXCT4-mgG-2 Induced Different Antibody Responses as Compared with HPA-mgG-2 Antigen after Vaccination Methods Mice were immunized intra-muscularly three times with HPA-mgG-2 or EXCT4-mgG-2 antigens at 10 day intervals. Serum was collected 3 weeks after the third immunization. IgG antibodies against the two different mgG-2 antigens were detected by indirect ELISA. Maxisorp 96 well plates were coated with antigens in carbonate buffer (pH 9.6) and for both assays the concentrations of the antigens were 0.5 µg/ml. A titration curve was created by three-fold dilutions of serum in PBS. Anti-mouse subclass-specific peroxidase-conjugated IgG were used as conjugates (Southern Biotech, US) at a 1:1000 dilution. The antibody reactivity was defined as optical density (OD) value derived for each subclass of IgG at a dilution which was close to the inflection point in the titration curve. Sera from unvaccinated mice were used as controls (n=10).

Statistics

Student's t-test (when normality test passed) or Mann-Whitney rank sum test was used for statistical calculations.

Results

Detection of Antibodies in Vaccinated Mice

The IgG1, IgG2b and IgG2c antibody levels were analyzed after intra muscular immunizations with HPA-mgG-2 or EXCT4-mgG-2 plus adjuvant. For HPA-mgG-2-immunized mice the antibody levels of IgG1 were similar in ELISA using HPA-mgG-2 or EXCT4-mgG-2 antigen (FIG. 6). For EXCT4-mgG-2-immunized mice the IgG1 antibody levels were significantly higher to EXCT4-mgG-2 antigen as compared with sera from HPA-mgG-2 immunized mice to HPA-mgG-2 antigen (P<0.001). In addition, sera from EXCT4-mgG-2 immunized mice were significantly higher against EXCT4-mgG-2 antigen as compared with HPA-mgG-2 antigen (P<0.001).

For HPA-mgG-2-immunized mice the antibody levels of IgG2b were similar to HPA-mgG-2 and EXCT4-mgG-2 antigen (FIG. 7). For EXCT4-mgG-2-immunized mice the IgG2b antibody levels in ELISA to EXCT4-mgG-2 antigen were similar as compared with sera from HPA-mgG-2-immunized mice to HPA-mgG-2 antigen. In contrast, sera from EXCT4-mgG-2-immunized mice were significantly higher to EXCT4-mgG-2 antigen as compared to HPA-mgG-2 antigen (P=0.011).

Figure 8:
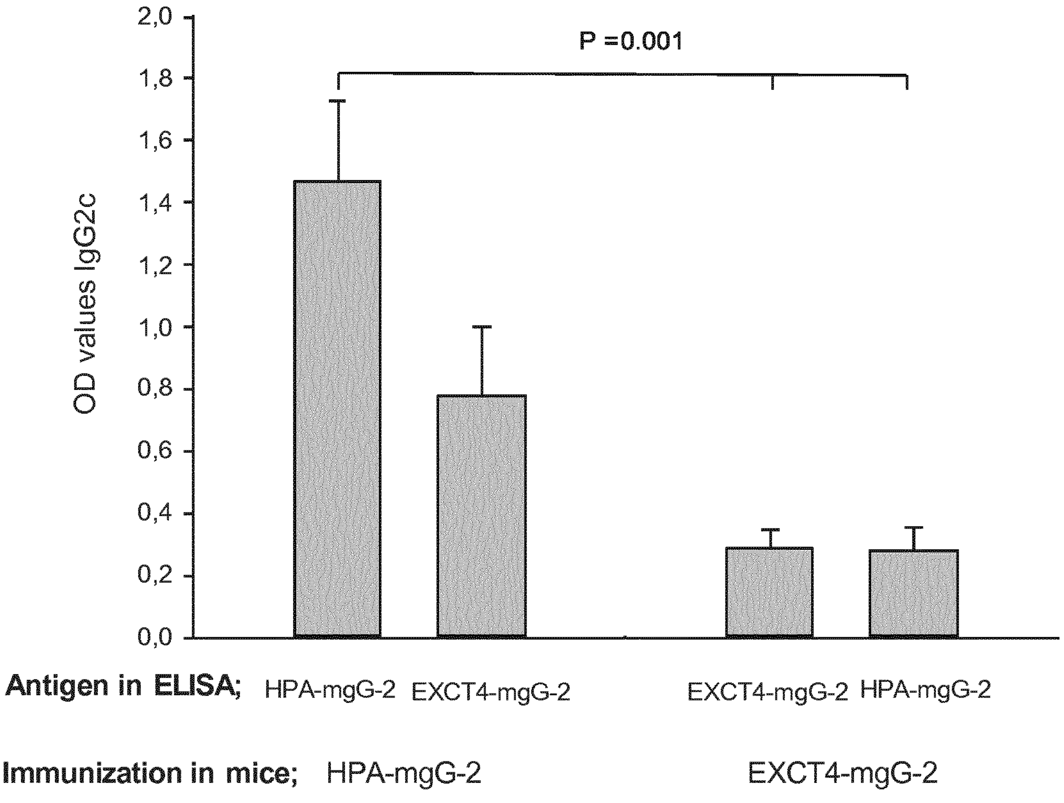
FIG. 8 shows anti-mgG-2 IgG2c antibody responses in serum. Mice were vaccinated with 1 μg of HPA-mgG-2 (n=10) or EXCT4-mgG-2 (n=10)×3 intra-muscularly with CpG and alum as adjuvant. Serum was collected 3 weeks after the third immunization and subjected to an mgG-2-specific ELISA using the same concentration of HPA-mgG-2 or EXCT4-mgG-2 antigen. Optical density values at 1/810 dilution were analyzed for both groups. Data are from two separate experiments. The error bars indicate mean+SEM.

For HPA-mgG-2-immunized mice the antibody levels of IgG2c were not statistically different in ELISA to HPA-mgG-2 as compared with EXCT4-mgG-2 antigen (FIG. 8). For EXCT4-mgG-2-immunized mice the IgG2c antibody levels to EXCT4-mgG-2 antigen and to HPA-mgG-2 antigen were significantly lower (P=0.001) as compared with sera from HPA-mgG-2 immunized mice to HPA-mgG-2 antigen.

Unvaccinated mice presented OD-values similar to the conjugate control wells (data not shown). We conclude that HPA-mgG-2 and EXCT4-mgG-2 immunized mice presented different antibody responses. As the adjuvant and immunization schedule were identical the differences are most likely dependent on the antigens which are presented differently to the immune system. For example, sera from EXCT4-mgG-2 immunized mice presented significantly higher IgG1 and IgG2b subclass reactivities to EXCT4-mgG-2 antigen as compared with HPA-mgG-2 antigen, indicating that the EXCT4-mgG-2 antigen elicited novel B-cell clones which produced antibodies binding to epitopes which were not recognized on the HPA-mgG-2 antigen.

Example 4

Recombinantly Produced EXCT4-mgG-2 Induces a Qualitatively Different Cellular Response as Compared with HPA-mgG-2 Antigen After Vaccination Methods T-Cell Proliferation Assay Mice were immunized intra-muscularly three times with 1 µg HPA-mgG-2 or EXCT4-mgG-2 antigens and CpG and alum as adjuvant at 10-day intervals. Three weeks after the last immunization, spleen cells were collected from three mice each from the HPA-mgG-2 immunized group, the EXCT4-mgG-2 immunized group and control mice group and pooled. CD4+ T-cells were purified (BD Bioscience) and a total of $2\times10^5$ CD4+ T-cells were obtained, including 20% splenocytes. In a parallel experiment only splenocytes were cultured and stimulated. The cells were plated in 96 well plates (Nunc) in Iscove's basal medium supplemented with 10% inactivated foetal bovine serum, 50 µM 2-mercaptoethanol and 2 mM L-glutamine. The cells were stimulated for 4 days with antigen (3 µg/ml) in triplicate and incubated at 37° C. in 5% $CO_2$. Proliferation was measured by radiolabeled thymidine (1 μCi, Amersham Biosciences) incorporation. The cells were harvested after 12 h additional incubation and run in a β-counter (1450 MicroBeta, Trilux) to measure the cell proliferation as counts per minute (cpm). The stimulation index (SI) was calculated from these values and values<3 was considered negative. As a positive control 2.5 μg/ml concanavalin A (Sigma Aldrich) was used.

Cytokine ELISA

Supernatants from the cell proliferation assay were collected at 96 hours (triplicates were pooled) and run in a cytokine ELISA for IFNγ (Duoset, R&D kit) according to the manufacturer's recommendations. Briefly, high binding 96 well plates (Greiner) were coated with capture antibody overnight at room temperature. Plates were blocked with 1% bovine serum albumin for 1 hour at 37° C. Standard and samples diluted 1:3 were added and incubated at room temperature for 3 h, after which biotinylated detection antibody was added. The plates were incubated overnight at 4° C. and streptavidin-horseradish peroxidase was added and the plates were developed with TMB, stopped with $H_2SO_4$ and read at 490 nm in a spectrophotometer.

Results

Figure 9:
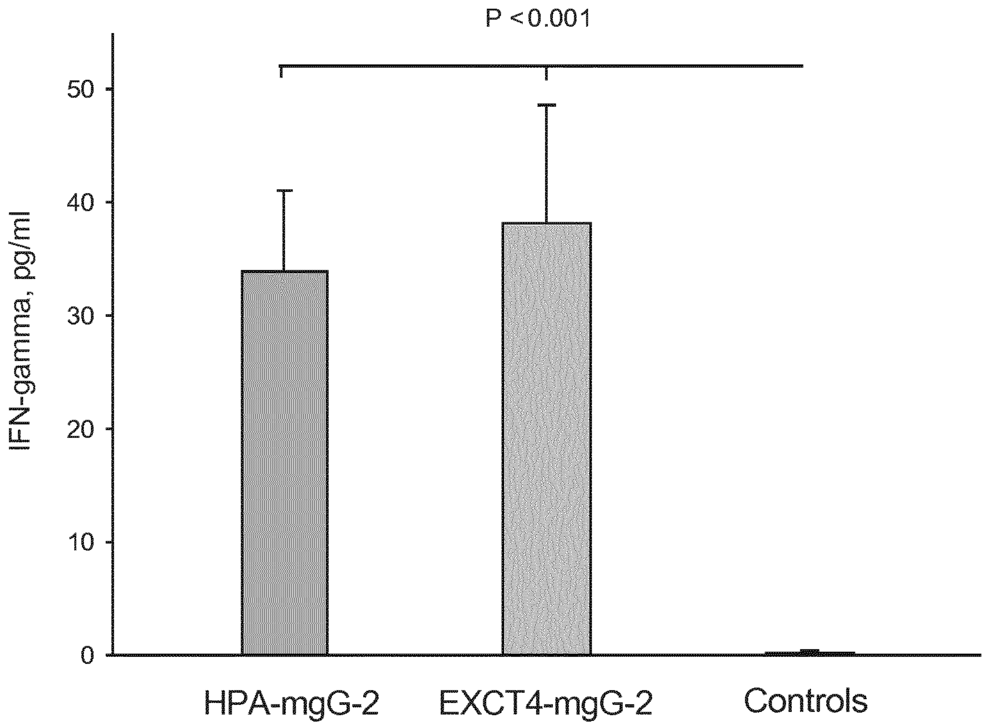
FIG. 9 shows interferon gamma (IFNγ) in vaginal washes at day 1 after challenge with 100,000 PFU of the HSV-2 strain 333. Mice were vaccinated with 1 μg of HPA-mgG-2 (n=10) or EXCT4-mgG-2 (n=10)×3 intra-muscularly with CpG and alum as adjuvant. Unvaccinated mice were used as controls. Data are from two separate experiments. The error bars indicate mean+SEM.

IFNγ was measured in vaginal washes at day 1 after challenge with 100,000 PFU of HSV-2 strain 333. Mice vaccinated with 1 μg of HPA-mgG-2 or EXCT4-mgG-2 3 times intra-muscularly with CpG and alum as adjuvant presented similar and significantly higher amounts as compared with unvaccinated controls (FIG. 9).

Both purified CD4+ T-cells and splenocytes from mice immunized with HPA-mgG-2 or EXCT4-mgG-2 were stimulated with antigen and proliferative responses (SI) were measured. HPA-mgG-2-immunized mice presented significantly higher SI (mean value 25.6) as compared with EXCT4-mgG-2 immunized mice (mean value 2.85), (FIG. 10A). Spleen cells from unvaccinated controls presented low SI (<3) for both antigens (data not shown).

IFNγ is known to be important in protection against genital herpes simplex infection in mice. IFNγ could be measured in supernatant from re-stimulated CD4+ T-cells from mice immunized with HPA-mgG-2 (8623 pg/ml) while low production (407 pg/ml) was detected for CD4+ T-cells collected from mice immunized with EXCT4-mgG-2. Similarly, higher levels of IFNγ, although not statistically significant, were detected when splenocytes from HPA-mgG-2-vaccinated mice were stimulated with HPA-mgG-2 (9300 pg/ml) as compared with IFNγ produced after vaccination with the EXCT4-mgG-2 antigen (6500 pg/ml). No IFNγ production could be detected in the control group. Taken together, these results show that the HPA-mgG-2 antigen after vaccination elicited a systemic CD4+ T-cell cellular immune response while the EXCT4-mgG-2 antigen induced only a systemic splenocytic IFNγ production distinct from the CD4+ T-cells. Thus, EXCT4-mgG-2 induces a qualitative different cellular response as compared with the cellular response after immunization with HPA-mgG-2.

Example 5

EXCT4-mgG-2 as a Diagnostic Antigen to Detect HSV-2 Infection

Methods

Antigens

The native entire mgG-2 protein was produced by HPA lectin affinity chromatography as described (Olofsson, S. et al., J Virol. 1981, vol. 38, 564; Liljeqvist, J. A. et al., J Gen Virol. 1998, vol. 79, 1215). The EXCT4-mgG-2 was produced as described in Example 1. A synthetic, 128 amino acid-long peptide was produced (LifeTein, US), containing amino acids 550-649 (portion of extracellular region) and 671-698 (entire intracellular (IC) region) of mgG-2. This portion of the extracellular region includes the immunodominant regions described by the inventor (Liljeqvist et al., 1998, J Gen Virol., vol. 79, 1215) and others, (Marsden et al., 1998, J Med Virol., vol. 56, 79; Grabowska et al., 1999, J Gen Virol., vol. 80, 1789; and Levi et al., 1996 Clin and Diagn. Lab Immunol., vol. 3, 265). The entire IC-region includes an antibody-binding region localized in the carboxy terminal end of mgG-2 (Grabowska et al., 1999, J Gen Virol., vol. 80, 1789; and Levi et al., 1996 Clin and Diagn Lab Immunol., vol. 3, 265). The peptide is designated Peptide-mgG-2 and has the sequence set forth in SEQ ID NO: 19.

Serum Samples

Sera were collected from clinical specimens received at the Department of Clinical Virology (Sahlgrenska University Hospital, Goteborg, Sweden). Four panels of sera were analyzed. Panel A consisted of 50 serum samples from patients with a culture-proven HSV-1 infection and with no detectable antibodies against HSV-2 by the Western blotting (WB) technique. Panel B consisted of 50 serum samples from patients with recurrent genital culture-proven HSV-2 infection that were WB positive for HSV-2. Panel C consisted of 50 serum samples which were HSV-1 and HSV-2 seronegative by ELISA with an HSV-1-derived type-common sodium deoxycholate-solubilized membrane preparation (Jeanson et al., 1983, J Clin Microbiol., vol. 18, 1160). Panel D consisted of 27 samples from a cohort of male blood donors from Tanzania which were WB negative for HSV-2 and interpreted as false positive in the FOCUS2 (HerpeSelect2) assay as described earlier (Görander et al., 2006, Clin Vaccine Immunol., vol. 13, 633).

Enzyme Immunoassays

HPA lectin-purified mgG-2 (HPA-mgG-2), used at present as a routine diagnostic antigen at the clinical Virology Laboratory at Sahlgrenska University Hospital, was coated in microtitre plates (Nunc) as described (Svennerholm et al., 1984, J Clin Microbiol., vol. 19, 235, and Liljeqvist et al., 1998, J Gen Virol., vol. 79, 1215). Both HPA-mgG-2 and EXCT4-mgG-2 were coated at a concentration of 0.16 μg/ml while the peptide was coated at a concentration of 10 μg/ml. Peroxidase-conjugated goat anti-human IgG, at a 1:1000 dilution (Jackson ImmunoResearch), was used as conjugate, with O-phenylenediamine as substrate. Each serum was tested at a 1:100 dilution. Cut-off for the HPA lectin-purified gG-2 antigen was defined as the mean absorbance value of an HSV-1-specific serum plus 0.2 OD units. The procedure for the HPA-mgG-2 ELISA and calculation of the cut-off value was identical as used for routine clinical samples. The cut-off for the EXCT4-mgG-2 and Peptide-mgG-2 ELISAs was defined as reactivity of negative samples plus 0.2 OD units. Each serum was classified as positive or negative.

Statistics

P values were calculated by two-tailed Fisher's exact test.

Results

The performance of the different mgG-2 antigens evaluated in an ELISA format using four well-defined serum panels, is shown in Table 1 below. The specificity of the herein claimed protein EXCT4-mgG-2 as antigen, is higher as compared with HPA-mgG-2 and Peptide-mgG-2 antigens in ELISA.

TABLE 1

| Serum panels | Antigen EXCT4-mgG-2 | HPA-mgG-2 | Peptide-mgG-2 |
|---|---|---|---|
| Panel A (HSV-1+) | 2/50 pos[A] | 6/50 pos | 10/50 pos[B] |
| Panel B (HSV-2+) | 47/50 pos | 47/50 pos | 44/50 pos |
| Panel C (HSV−) | 2/50 pos | 0/50 pos | 1/50 pos |
| Panel D (HSV-2-negative blood donors, Tanzania) | 0/27 pos[C] | 6/27 pos[D] | 12/27 pos[E] |

Statistical significances are as follows:
P = 0.028 for A versus B,
P = 0.029 C versus D,
P = 0.0001 C versus E.

The invention claimed is:

1. A protein comprising a truncated version of the herpes simplex virus 2 (HSV-2) protein membrane-bound glycoprotein G (mgG-2), said protein comprising:

(i) an extracellular region of mgG-2 (EX-mgG-2), or a truncated version thereof, wherein said extracellular region EX-mgG-2 comprises at least 290 amino acids and has at least 95% sequence identity (% SI) to SEQ ID NO: 3;

(ii) a truncated transmembrane region of mgG-2 (t-TMR-mgG-2), wherein said truncated transmembrane region t-TMR-mgG-2 comprises 4 or 5 amino acids and has at least 80% sequence identity to SEQ ID NO: 12; and (iii) an intracellular region of mgG-2 (IC-mgG-2), or a truncated version thereof, wherein said intracellular region IC-mgG-2 comprises at least 26 amino acids and has at least 90% sequence identity to SEQ ID NO: 8.

2. The protein according to claim 1, wherein the truncated transmembrane region (t-TMR-mgG-2) has the amino acid sequence of SEQ ID NO: 7.

3. The protein according to claim 1, wherein the extracellular region of mgG-2 (EX-mgG-2) is truncated.

4. The protein according to claim 3, wherein the truncated extracellular region of mgG-2 (EX-mgG-2) shares at least 97% sequence identity in with SEQ ID NO: 3.

5. The protein according to claim 1, wherein the intracellular region of mgG-2 (IC-mgG-2) is truncated.

6. The protein according to claim 5, wherein the truncated intracellular region of mgG-2 (IC-mgG-2) shares at least 95% sequence identity with SEQ ID NO: 8.

7. The protein according to claim 1, wherein said protein comprises:

(i) amino acids 345-649 of the extracellular region of mgG-2;

(ii) amino acids 667-670 of the TMR of mgG-2; and (iii) amino acids 671-698 of the intracellular region of mgG-2;

wherein the extracellular region of mgG2 has the amino acid sequence set forth in SEQ ID NO:3; the TMR of mgG2 has the amino acid sequence set forth in SEQ ID NO:7; and the intracellular region of mgG2 has the amino acid sequence set forth in SEQ ID NO: 8.

8. A protein EXCT4-mgG-2, having an amino acid sequence as defined in SEQ ID NO: 5, or an amino acid sequence with at least 90% sequence identity to SEQ ID NO: 5.

9. A pharmaceutical composition comprising a protein as defined in claim 1, together with one or more components selected from the group consisting of adjuvants, stabilizers, buffers, surfactants, salts and preservatives.

10. An HSV-2 vaccine comprising a protein as defined in claim 1.

11. An HSV-2 vaccine comprising the protein EXCT4-mgG-2, wherein said protein EXCT4-mgG-2 has an amino acid sequence as defined in SEQ ID NO:5.

12. The HSV-2 vaccine according to claim 10, comprising an effective dose of 0.5-1000 μg of the protein.

13. A method for the treatment and/or prevention of disease related to an HSV 2 infection, whereby a protein as defined in claim 1 is administered to a subject in need of such treatment and/or prevention.

14. The HSV-2 vaccine according to claim 12, wherein the effective dose of the protein is 20-200 μg.

15. The HSV-2 vaccine according to claim 12, wherein the effective dose of the protein is 50-100 μg.

16. The method of claim 13, wherein said method further comprises the administration of a second HSV-2 glycoprotein to said subject.

17. The method of claim 16, wherein said second HSV-2 glycoprotein is selected from any one of gB, gC, gD, gE, gH, gI, gK, gL, and gM, and fragments thereof.

18. The method of claim 16, wherein said method further comprises the administration of an HSV non-glycoprotein to said subject.

19. The method of claim 18, wherein said HSV non-glycoprotein is selected from any one of UL11, UL14, UL16, UL17, UL21, UL36, UL37, UL41, UL46, UL48, UL49, US6, US7, US8, US11, VP13/14, VP16, VP22, VP5, VP19c, VP21, VP23, VP24, and VP26.

* * * * *